(12) United States Patent
Heller et al.

(10) Patent No.: US 7,704,726 B2
(45) Date of Patent: *Apr. 27, 2010

(54) ACTIVE PROGRAMMABLE MATRIX DEVICES

(75) Inventors: Michael James Heller, Encinitas, CA (US); James Patrick O'Connell, Del Mar, CA (US); Robert David Juncosa, Mission Viejo, CA (US); Ronald George Sosnowski, Coronado, CA (US); Thomas Ratcliffe Jackson, San Diego, CA (US)

(73) Assignee: Gamida For Life B.V., Rotterdam (NL)

( * ) Notice: Subject to any disclaimer, the term of this patent is extended or adjusted under 35 U.S.C. 154(b) by 455 days.

This patent is subject to a terminal disclaimer.

(21) Appl. No.: 11/505,679

(22) Filed: Aug. 17, 2006

(65) Prior Publication Data

US 2007/0054299 A1 Mar. 8, 2007

Related U.S. Application Data

(63) Continuation of application No. 09/597,866, filed on Jun. 20, 2000, now Pat. No. 7,101,661, which is a continuation of application No. 09/141,286, filed on Aug. 27, 1998, now Pat. No. 6,245,508, which is a continuation of application No. 08/534,454, filed on Sep. 27, 1995, now Pat. No. 5,849,486, which is a continuation-in-part of application No. 08/304,657, filed on Sep. 9, 1994, now Pat. No. 5,632,957.

(51) Int. Cl.
*C12M 1/36* (2006.01)
*G01N 15/06* (2006.01)

(52) U.S. Cl. ............... 435/283.1; 435/287.2; 422/68.1; 422/82.01

(58) Field of Classification Search .............. None
See application file for complete search history.

(56) References Cited

U.S. PATENT DOCUMENTS

| 3,950,738 A | 4/1976 | Hayashi et al. |
| 3,995,190 A | 11/1976 | Salgo |
| 4,225,410 A | 9/1980 | Pace |
| 4,283,773 A | 8/1981 | Daughton et al. |

(Continued)

FOREIGN PATENT DOCUMENTS

EP 0228075 B1 4/1991

(Continued)

OTHER PUBLICATIONS

Abrams et al, "Comprehensive Detection of Single Base Changes in Human Genomic DNA Using Denaturing Gradient Gel Electrophoresis & A GC Clamp", Genomics, 7, 1990, 463-475.

(Continued)

*Primary Examiner*—B J Forman
(74) *Attorney, Agent, or Firm*—John P. White; Cooper & Dunham LLP

(57) ABSTRACT

A system for performing molecular biological diagnosis, analysis and multistep and multiplex reactions utilizes a selfaddressable, selfassembling microelectronic system for actively carrying out controlled reactions in microscopic formats. The device includes a power supply and waveform generator adapted to supply a DC bias and superimposed AC signal to the system through an interface to the array of microlocations.

5 Claims, 15 Drawing Sheets

U.S. PATENT DOCUMENTS

| | | | |
|---|---|---|---|
| 4,537,861 A | 8/1985 | Elings et al. | |
| 4,563,419 A | 1/1986 | Ranki et al. | |
| 4,580,895 A | 4/1986 | Patel | |
| 4,584,075 A | 4/1986 | Goldstein et al. | |
| 4,594,135 A | 6/1986 | Goldstein | |
| 4,661,451 A | 4/1987 | Hansen | |
| 4,731,325 A | 3/1988 | Palva et al. | |
| 4,751,177 A | 6/1988 | Stabinsky | |
| 4,787,963 A | 11/1988 | MacConnell | |
| 4,807,161 A | 2/1989 | Comfort et al. | |
| 4,816,418 A | 3/1989 | Mack et al. | |
| 4,822,566 A | 4/1989 | Newman | |
| 4,828,979 A | 5/1989 | Klevan et al. | |
| 4,908,112 A | 3/1990 | Pace | |
| 4,909,919 A * | 3/1990 | Morris et al. | 204/603 |
| 4,936,963 A | 6/1990 | Mandecki et al. | |
| 5,063,081 A | 11/1991 | Cozzette et al. | |
| 5,064,519 A | 11/1991 | Tice, Jr. et al. | |
| 5,074,977 A | 12/1991 | Cheung et al. | |
| 5,075,077 A | 12/1991 | Durley, III et al. | |
| 5,096,669 A | 3/1992 | Lauks et al. | |
| 5,096,807 A | 3/1992 | Leaback | |
| 5,110,434 A | 5/1992 | Zhu et al. | |
| 5,114,674 A | 5/1992 | Stanbro et al. | |
| 5,125,748 A | 6/1992 | Bjornson et al. | |
| 5,126,022 A | 6/1992 | Soane et al. | |
| 5,143,854 A | 9/1992 | Pirrung et al. | |
| 5,164,319 A | 11/1992 | Hafeman et al. | |
| 5,166,063 A | 11/1992 | Johnson | |
| 5,200,051 A | 4/1993 | Cozzette et al. | |
| 5,202,231 A | 4/1993 | Drmanac et al. | |
| 5,219,726 A | 6/1993 | Evans | |
| 5,227,265 A | 7/1993 | DeBoer et al. | |
| 5,234,566 A | 8/1993 | Osman et al. | |
| 5,242,797 A | 9/1993 | Hirschfeld | |
| 5,304,487 A | 4/1994 | Wilding et al. | |
| 5,312,527 A | 5/1994 | Mikkelsen et al. | |
| 5,324,633 A | 6/1994 | Fodor et al. | |
| 5,433,819 A | 7/1995 | McMeen | |
| 5,434,049 A | 7/1995 | Okano et al. | |
| 5,436,129 A | 7/1995 | Stapleton | |
| 5,445,525 A | 8/1995 | Broadbent et al. | |
| 5,445,934 A | 8/1995 | Fodor et al. | |
| 5,464,517 A | 11/1995 | Hjerten et al. | |
| 5,468,646 A | 11/1995 | Mattingly et al. | |
| 5,516,698 A | 5/1996 | Begg et al. | |
| 5,527,670 A | 6/1996 | Stanley | |
| 5,532,129 A | 7/1996 | Heller | |
| 5,565,322 A | 10/1996 | Heller | |
| 5,593,838 A | 1/1997 | Zanzucchi et al. | |
| 5,605,662 A | 2/1997 | Heller et al. | |
| 5,632,957 A | 5/1997 | Heller et al. | |
| 5,653,939 A | 8/1997 | Hollis et al. | |
| 5,660,701 A | 8/1997 | Grushka et al. | |
| 5,667,667 A | 9/1997 | Southern | |
| 5,681,751 A | 10/1997 | Begg et al. | |
| 5,726,026 A | 3/1998 | Wilding et al. | |
| 5,744,305 A | 4/1998 | Fodor et al. | |
| 5,750,015 A | 5/1998 | Soane et al. | |
| 5,766,960 A | 6/1998 | Cornell et al. | |
| 5,776,677 A | 7/1998 | Tsui et al. | |
| 5,789,167 A | 8/1998 | Konrad | |
| 5,837,859 A | 11/1998 | Teoule et al. | |
| 5,846,708 A | 12/1998 | Hollis et al. | |
| 5,849,486 A | 12/1998 | Heller et al. | |
| 5,853,668 A | 12/1998 | Begg et al. | |
| 5,965,452 A | 10/1999 | Kovacs | |
| 6,013,166 A | 1/2000 | Heller | |
| 6,017,696 A | 1/2000 | Heller | |
| 6,048,690 A | 4/2000 | Heller et al. | |
| 6,051,380 A | 4/2000 | Sosnowski et al. | |
| 6,054,270 A | 4/2000 | Southern | |
| 6,245,508 B1 | 6/2001 | Heller et al. | |
| 6,582,660 B1 * | 6/2003 | Heller et al. | 422/68.1 |
| 7,101,661 B1 | 9/2006 | Heller et al. | |

FOREIGN PATENT DOCUMENTS

| | | |
|---|---|---|
| GB | 2247889 A | 3/1992 |
| WO | WO 86/03782 A1 | 7/1986 |
| WO | WO 90/01564 A1 | 2/1990 |

OTHER PUBLICATIONS

Anand et al, "Pulsed Field Gel Electrophoresis, Gel Electrophoresis of Nucleic Acids—A Practical Approach", 2d ed, eds. D.Rickman & B.D. Hames (NY: IRL Press), 101-123.

Anderson et al, "Quantitative Filter Hybridization, Nucleic Acid Hybridizaton—A Practical Approach", 2d ed, D.Rickwood & B.D. Hames (Washington D.C.: IRL Press), 1985, 73-111.

Bains, "Setting a Sequence to Sequence a Sequence", Bio/Technology, 10, 1992, 757-758.

Baringa, "Will 'DNA Chip' Speed Genome Initiative?", Science, 253, Sep. 27, 1991, 1489.

Beattie et al, "Genosensor Technology, The 1992 San Diego Conference: Genetic Recognition", Nov. 1992, 1-5.

Beltz et al, "Isolation of Multigene Families & Determination of Homologies by Filter Hybridization Methods", Methods in Enzymology, 100, 1983, 266-285.

Brown et al, "Electrochemically Induced Adsorption of Radio-Labelled DNA on Gold & HOPG Substrates for STM Investigations", Ultramicroscopy, 38, 1991, 253-264.

Conner et al, "Detection of Sickle Cell [3]-Globin Allele by Hybridization With Synthetic Oligonucleotides", Proc. Natl. Acad. Sci. USA, 80, Jan. 1983, 273-282.

Drmanac et al, "DNA Sequence Determination by Hybridization: A Strategy for Efficient Large Scale Sequencing" Science, 260, Jun. 11, 1993, 1649-1652.

Drmanac et al, "Sequencing of Megabase Plus DNA by Hybridization: Theory of the Method", Genomics, 4, 1989, 114-128.

Edman, et al., "Electric Field Directed Nucleic Acid Hybridization on Microchips", Nucleic Acids Research, 1977, 25, 24, 4907-4914.

Eggers et al, "Biochip Technology Development", Lincoln Lab, Technical Report 901, Nov. 9, 1990.

Fiaccabrino et al, "Arrays of Individually Addressable Microelectrodes", Sensors & Actuators B. 18-19, 1994, 675-677.

Fodor et al, "Light Directed, Spatially Addressable Parallel Chemical Synthesis", Science, 251, 1991, 767-773.

Fodor et al, "Multiplexed Biochemical Assays With Biological Chips", Nature, 364, Aug. 5, 1993, 555-556.

Foulds, et al., "Biosensors: Current Applications and Future Potential", BioEssays, 3, 3, Sep. 1985, 129-132.

Gildea, et al., "A Versatile Acid Labile-Linker for Modification of Synthetic Biomolecules", Tetrahedron Letters, 31, 49, Nov. 1990, 7095-7098.

Heller et al, "Intramolecular Catalysis of Acylation & Deacylation in Peptides Containing Cysteine & Histidine" , Journal of the American Chemical Society, 99, 8, Apr. 13, 1977, 2780-2785.

Horejsi et al, "Determination of Dissociation Constants of Lectin Sugar Complexes by Means of Affinity Electrophoresis", Biochimica et Biophysical Acta, 499, 1977, 290-300.

Horejsi, "Some Theoretical Aspects of Affinity Electrophoresis", Journal of Chromatography, 178, 1979, 1-13.

Kakerow et al, "A Monolithic Sensor Array of Individually Addressable Microelectrodes", Sensors & Actuators B, 43, 1994, 296-301.

Livache, et al., "Polypyrrole DNA Chip on a Silicon Device: Example of Hepatitis C Virus Genotyping", Analytical Biochemistry, 255, 1998, 188-194.

Mandecki, et al., "High Resolution Polyacrylamide Gel Electrophoresis of Oligonucleotides Using L-Histidine Buffer", DNA, 7, 1, 1988, 57-62.

Mathews et al, "Analytical Strategies for the Use of DNA Probes", Analytical Biochemistry, 169, 1988, 1-25.

Meo, et al., "Monoclonal Antibody to the Message Sequence Tyr-Gly-Gly-Phe of Opioid Peptides Exhibits the Specificity Requirements of Mammalian Opioid Receptors", Proc. Natl. Acad. Sci. USA, 80, Jul. 1983, 4084-4088.

Merrifield, "Solid Phase Peptide Synthesis. I. The Synthesis of a Tetrapeptide", Journal of the American Chemical Society, 85, 13, Jul. 5, 1963, 2149-2154.

Palecek, "New Trends in Electrochemical Analysis of Nucleic Acids", Bioelectrochemistry & Bioenergetics, 20, 1988, 179-194.

Ranki et al, "Sandwich Hybridization As a Convenient Method for the Detection of Nucleic Acids in Crude Samples", Gene, 21, 1983, 77-85.

Saiki, "Amplification of Genomic DNA, PCR Protocols: A Guide to Methods & Applications", Academic Press, Inc., 1990, 13-20.

Sosnowski, et al. "Rapid Determination of Single Base Mismatch Mutations in DNA Hybrids by Direct Electric Field Control", Proc. Natl. Acad. Sci. USA, 94, Feb. 1997, 1119-1123.

Southern et al, "Analyzing & Comparing Nucleic Acid Sequences by Hybridization to Arrays of Oligonucleotides Evaluation Using Experimental Models", Genomics, 13, 1992, 1008-1017.

Strezoska et al, "DNA Sequencing by Hybridization: 100 Bases Read by a Non-Gel Based Method", Proc. Natl. Acad. Sci. USA, 88, 1991, 10089-10093.

Wallace et al, "Hybridization of Synthetic Oligodedexribonucleotides to x 174 DNA: The Effect of Single Base Pair Mismatch", Nucleic Acids Research, 6, 1979, 3543-3557.

Washizu, "Electrostatic Manipulation of Biological Objects", Journal of Electrostatics, 25, 1990, 109-123.

Washizu et al, "Electrostatic Manipulation of DNA in Microfabricated Structures", IEEE Transactions on Industry Applications, 26, 6, Nov.-Dec. 1990, 1165-1172.

"Le Principe de l'hybridation", Le Technoscope de Biofutur, 166, Apr. 1997, 3.

* cited by examiner

SEQUENCE LISTING

<160> NUMBER OF SEQ ID NOS: 2

<210> SEQ ID NO 1
<211> LENGTH: 17
<212> TYPE: DNA
<213> ORGANISM: Homo sapiens
<220> FEATURE:
<221> NAME/KEY: misc_feature
<222> LOCATION: (1)..(17)
<223> OTHER INFORMATION: Nucleotide 1 is modified with Bodipy Texas Red

<400> SEQUENCE: 1
aaattttaat atataat                                              17

<210> SEQ ID NO 2
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: Nucleotide 1 is modified with Bodipy Texas Red

<400> SEQUENCE: 2
ccacgtagaa ctgctcatc                                            19

ACTIVE PROGRAMMABLE MATRIX DEVICES

RELATED APPLICATION INFORMATION

This application is a continuation of U.S. application Ser. No. 09/597,866, filed Jun. 20, 2000, entitled "APPARATUS FOR ACTIVE PROGRAMMABLE MATRIX DEVICES," now issued as U.S. Pat. No. 7,101,661, which is a continuation of U.S. application Ser. No. 09/141,286, filed Aug. 27, 1998, entitled "METHOD FOR FINGERPRINTING UTILIZING AN ELECTRONICALLY ADDRESSABLE ARRAY," issued as U.S. Pat. No. 6,245,508, which is a continuation of U.S. application Ser. No. 08/534,454, filed Sep. 27, 1995, entitled "METHODS FOR HYBRIDIZATION ANALYSIS UTILIZING ELECTRICALLY CONTROLLED HYBRIDIZATION," issued as U.S. Pat. No. 5,849,486, which is a continuation-in-part of application Ser. No. 08/304,657, filed Sep. 9, 1994, entitled "MOLECULAR BIOLOGICAL DIAGNOSTIC SYSTEM," issued as U.S. Pat. No. 5,632,957.

FIELD OF THE INVENTION

This invention relates to devices and systems for performing multi-step molecular biological type diagnostic analyses in multiplex formats. More particularly, the molecular biological type analyses include various nucleic acid hybridizations reactions and associated biopolymer synthesis. Additionally, antibody/antigen reactions and other clinical diagnostics can be performed.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual,* 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps (see FIG. 1). In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microliter plate, etc.).

A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out the polymerase chain reaction (PCR) or other amplification procedure. The PCR procedure amplifies (increases) the number of target DNA sequences. Amplification of target DNA helps to overcome problems related to complexity and sensitivity in genomic DNA analysis. All these procedures are time consuming, relatively complicated, and add significantly to the cost of a diagnostic test. After these sample preparation and DNA processing steps, the actual hybridization reaction is performed. Finally, detection and data analysis convert the hybridization event into an analytical result.

The steps of sample preparation and processing have typically been performed separate and apart from the other main steps of hybridization and detection and analysis. Indeed, the various substeps comprising sample preparation and DNA processing have often been performed as a discrete operation separate and apart from the other substeps. Considering these substeps in more detail, samples have been obtained through any number of means, such as obtaining of full blood, tissue, or other biological fluid samples. In the case of blood, the sample is processed to remove red blood cells and retain the desired nucleated (white) cells. This process is usually carried out by density gradient centrifugation. Cell disruption or lysis is then carried out, preferably by the technique of sonication, freeze/thawing, or by addition of lysing reagents. Crude DNA is then separated from the cellular debris by a centrifugation step. Prior to hybridization, double-stranded DNA is denatured into single-stranded form. Denaturation of the double-stranded DNA has generally been performed by the techniques involving heating (>TM), changing salt concentration, addition of base (NaOH), or denaturing reagents (urea, formamide, etc.). Workers have suggested denaturing DNA into its single-stranded form in an electrochemical cell. The theory is stated to be that there is electron transfer to the DNA at the interface of an electrode, which effectively weakens the double-stranded structure and results in separation of the strands. See, generally, Stanley, "DNA Denaturation by an Electric Potential", U.K. patent application 2,247,889 published Mar. 18, 1992.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR). (See, M. A. Innis et al, PCR Protocols: A Guide to Methods and AADlications, Academic Press, 1990). While amplification results in an enormous number of target nucleic acid sequences that improves the subsequent direct probe hybridization step, amplification involves lengthy and cumbersome procedures that typically must be performed on a stand alone basis relative to the other substeps. Substantially complicated and relatively large equipment is required to perform the amplification step.

The actual hybridization reaction represents the most important and central step in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266-308, 1985). One format, the so-called "dot blot" hybridization, involves the non-covalent attachment of target DNAs to filter, which are subsequently hybridized with a radioisotope labelled probe(s). "Dot blot" hybridization gained wide-spread use, and many versions were developed (see M. L. M. Anderson and B. D. Young, in *Nucleic Acid Hybridization—A Practical Approach*, B. D. Hames and S. J. Higgins, Eds., IRL Press, Washington; D.C. Chapter 4, pp. 73-111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Barinaga, 253 Science, pp. 1489, 1991; W. Bains, 10 Bio/Technology, pp. 757-758, 1992). These methods usually attach specific DNA sequences to very small specific areas of a solid support, such as micro wells of a DNA chip. These hybridization formats are micro-scale versions of the conventional "dot blot" and "sandwich" hybridization systems.

The micro-formatted hybridization can be used to carry out "sequencing by hybridization" (SBH) (see M. Barinaga, 253 Science, pp. 1489, 1991; W. Bains, 10 Bio/Technology, pp. 757-758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1992; and R. Dramanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649-1652, 1993, used the second format to sequence several short (116 bp) DNA sequences. Target DNAs were attached to membrane supports ("dot blot" format). Each filter was sequentially hybridized with 272 labelled 10-mer and 11-mer oligonucleotides. A wide range of stringency condition was used to achieve specific hybridization for each n-mer probe; washing times varied from 5 minutes to overnight, and temperatures from 0° C. to 16° C. Most probes required 3 hours of washing at 16° C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorometrically, calorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

In conventional fluorometric detection systems, an excitation energy of one wavelength is delivered to the region of interest and energy of a different wavelength is reemitted and detected. Large scale systems, generally those having a region of interest of two millimeters or greater, have been manufactured in which the quality of the overall system is not inherently limited by the size requirements of, the optical elements or the ability to place them in optical proximity to the region of interest. However, with small geometries, such as those below 2 millimeters, and especially those on the order of 500 microns or less in size of the region of interest, the conventional approaches to fluorometer design have proved inadequate. Generally, the excitation and emission optical elements must be placed close to the region of interest. Preferably, a focused spot size is relatively small, often requiring sophisticated optical designs. Further, because it is usually desirable to maximize the detectable area, the size of the optical components required to achieve these goals in relation to their distance from the region of interest becomes important, and in many cases, compromises the performance obtained. Accordingly, a need exists for an improved fluorescent detection system.

Attempts have been made to combine certain processing steps or substeps together. For example, various microrobotic systems have been proposed for preparing arrays of DNA probe on a support material. For example, Beattie et al., in *The 1992 San Diego Conference: Genetic Recognition*, November, 1992, used a microrobotic system to deposit micro-droplets containing specific DNA sequences into individual microfabricated sample wells on a glass substrate.

Generally, the prior art processes have been extremely labor and time intensive. For example, the PCR amplification process is time consuming and adds cost to the diagnostic assay. Multiple steps requiring human intervention either during the process or between processes is suboptimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, numerous attempts have been made to provide effective techniques to conduct multi-step, multiplex molecular biological reactions. However, for the reasons stated above, these techniques are "piece-meal" and limited. These various approaches are not easily combined to form a system which can carry out a complete DNA diagnostic assay. Despite the long-recognized need for such a system, no satisfactory solution has been proposed previously.

SUMMARY OF THE INVENTION

The present invention relates to the design, fabrication, and uses of a self-addressable self-assembling microelectronic devices and systems which can actively carry out controlled multi-step processing and multiplex reactions in a microscopic formats. These reactions include, but are not limited to, most molecular biological procedures, such as nucleic acid hybridization, antibody/antigen reaction, and related clinical diagnostics. In addition, the claimed devices and systems are able to carry out multi-step combinatorial biopolymer synthesis, including, but not limited to, the synthesis of different oligonucleotides or peptides at specific micro-locations on a given device.

The claimed devices and systems are fabricated using both microlithographic and micro-machining techniques. The basic device has a matrix of addressable microscopic locations on its surface; each individual micro-location is able to control electronically and direct the transport and attachment of specific binding entities (e.g., nucleic acids, enzymes, antibodies) to itself. All microlocations can be addressed with their specific binding entities. The self-addressing process requires minimal outside intervention in terms of fluidics or mechanical components.

The device is able to control and actively carry out a variety of assays and reactions. Analytes or reactants can be transported by free field electrophoresis to any specific microlocation where the analytes or reactants are effectively concentrated and reacted with the specific binding entity at the micro-location. In the case of hybridization analysis, the sensitivity for detecting a specific analyte or reactant is improved because hybridization reactants are concentrated at a specific microscopic location. Any unbound analytes or reactants can be removed by reversing the polarity of a micro-location. Thus, the device also improves the specificity of the reactions. Basic devices for nucleic acid hybridization and other analyses are alternatively referred to as APEX devices, which stands for addressable programmable electronic matrix.

In one aspect of this invention, the APEX device is utilized with a fluidic system in which a sample is flowed over the APEX device during operation. In the preferred embodiment, the fluidic system includes a flow cell and a liquid-waste containment vessel. The sample is provided to the input to the flow cell and directed across the active areas of the APEX system. Preferably, a defined volume is provided within the flow cell, preferably in the range from 5 to 10 microliters. A flowing sample over the active detection device provides important advantages in the hybridization analysis of dilute, concentrated and/or relatively complex DNA samples. For example, if the total sample volume is relatively large compared to the same chamber volume, flowing of the sample provides more complete analysis of the entire sample. Alternatively, where the sample volume is relatively small, and/or the DNA is relatively concentrated, dilution is indicated in order to reduce the viscosity of the sample.

In another aspect of the invention, additional processing steps or substeps may be performed in sequence with a "system". The system is an integrated arrangement of component devices. Each component device is appropriately designed and scaled to carry out a particular function. In its most complete embodiment, a system may perform all aspects of sample preparation, hybridization and detection and analysis. In this fullest form, the sample is first prepared, such as by an electronic cell sorter component. Generally, electronic refers more specifically to the ability of the component device to electrophoretically transport charged entities to or from itself. Further DNA processing and complexity reduction may optionally be performed by a crude DNA selector component, and a restriction fragment selector component.

The final processed target DNA is transported to the analytical component where electronic hybridization analysis is carried out in a microscopic multiplex format. This analytical component device is also referred to as the APEX or analytical chip. Associated detection and image analysis components provide the results.

Within the system materials may optionally be transported between components (devices) by free field electrophoresis, channeling, fluidics or other techniques. Optionally, electronic reagent dispenser components can provide electrophoretic transport of reagents to the various processing components of the system. Optionally, an electronic waste disposal system may be formed by providing an electrode and charged matrix material that attracts and holds charged waste products. Optionally, an electronic DNA fragment storage system can serve to temporarily hold other DNA fragments for later hybridization analysis.

In one aspect of this invention, genomic DNA complexity reduction is performed by processes that isolate those specific DNA fragments containing the desired target sequence from the bulk of the DNA material that lacks the desired target sequence. Crude DNA can be transported and captured on a support material. The bound DNA can then be severed using appropriate restriction enzymes. After severing, the DNA fragments can be transported to a component device that selectively hybridizes specific DNA fragments. Those fragments that contain the actual target sequences to be analyzed can be selectively released, via further restriction enzyme cleavage, and transported to the analytical component (APEX chip) of the system. Optionally, this procedure may be repeated for other fragments containing other target sequences.

A controller for the device (or system) provides for individual control of various aspects of the device. When an APEX device or chip containing addressable microscopic locations is utilized, the controller permits individual microlocations to be controlled electronically so as to direct the transport and attachment of specific binding entities to that location. The device may carry out multi-step and multiplex reactions with complete and precise electronic control, preferably under control of a microprocessor based component. The rate, specificity, and sensitivity of multi-step and multiplex reactions are greatly improved at the specific microlocations on the device. The controller interfaces with a user via input/output devices, such as a display and keyboard input. Preferably, a graphical user interface is adapted for ease of use. The input/output devices are connected to a controller, which in turn controls the electrical status of the addressable electronic locations on the system. Specifically, the controller directs a power supply/waveform generator to generate the electronic status of the various microlocations. Optionally, an interface is used between the power supply/waveform generator and the APEX device or system. The interface preferably comprises a bank of relays subject to the controller via a multifunction input/output connection. The relays preferably serve to connect the power supply/waveform generator to the APEX device by controlling the connection as to its polarity, the presence or absence of a connection and the amount of potential or current supply to the individual location. The controller preferably controls the illumination source directed at the hybridization system. A detector, image processing and data analysis system are optically coupled to the APEX device. In the preferred embodiment, a fluorescent microscope receives and magnifies the image from the hybridization events occurring on the various micro-locations of the device. The emissions are optically filtered and detected by a charge coupled device (CCD) array or microchannel plate detector. The image is then stored and analyzed. Preferably, the results are displayed to the user on the monitor.

In one aspect of this invention, an improved apparatus for the detection of fluorescence in small geometry systems is utilized. In the preferred embodiment, a light transfer member, such as an optical fiber, is disposed within a light guide path disposed between the region of interest and the detector. In the most preferred embodiment, a fiber optic is coaxially arranged in a liquid light guide. An excitation source, such as a laser, provides radiation through optics such that the excitation fiber delivers the excitation radiation to the region of interest. Preferably, the excitation fiber is disposed axially within the return light guide path, at least at the proximal end adjacent the region of interest. The return path preferably comprises a liquid light guide preferably including optics to receive emission from the region of interest, and to transfer that emission through the light guide to the detector.

In another aspect of this invention, the hybridization system is formed having a plurality of microlocations formed atop a substrate containing control electronics. Specifically, switching circuits are provided to address individually the microlocations. The electrical connections are made via the backside relative to where sample contact is to be made. Additionally, an optical pathway, such as a waveguide, is disposed beneath the microlocation to permit backside access to the microlocation. Optical excitation, if necessary, may be directed to the microlocation via the waveguide. Detection of emitted radiation may be detected via the backside waveguide. In yet another aspect of this invention, a sample containment system is disposed over the system, particularly the hybridization matrix region. In the preferred embodiment, the matrix hybridization region (including sample containment component) is adapted for removal from the remainder of the device providing the electronic control and detector elements.

In another aspect of this invention, improved processes for forming a matrix hybridization system are described. In one process, a substrate, such as silicon, is formed with an insulating layer, such as a thick oxide. Conductive microlocations are formed, such as by deposition of metal (e.g., aluminum or gold) that is then patterned, such as by conventional photolithographic techniques. An insulating coating is formed, such as TEOS formed by PECVD. Optionally, a nitride passivation coating is formed over the TEOS layer. Openings to the microelectrode are formed through the nitride and glass. Optionally, adhesion improving materials such as titanium tungsten may be utilized in connection with the metal layer to promote adhesion to the oxide and/or glass. In yet a further improvement, wells may be formed atop of the electrode by undercutting a nitride layer disposed on an oxide layer supported by the substrate.

Electronic control of the individual microlocations may be done so as to control the voltage or the current. When one aspect is set, the other may be monitored. For example, when voltage is set, the current may be monitored. The voltage and/or current may be applied in a direct current mode, or may vary with time. For example, pulsed currents or DC biases may be advantageously utilized. The pulsed system may be advantageously utilized with the fluidic system, especially the flow cell design. By coordinating the pulse sequence and flow rate, the sample can be more effectively interrogated throughout the sample volume. Additionally, even for non-flow situations, such as where there are relatively high amounts of non-target material, e.g., DNA, which without pulsing might overwhelm the activated test sites. Pulse techniques generally result in higher target mobility rates at higher ionic strength, reduced probe burn-out effects, improved hybridization efficiencies, improved discrimination of point mutations and enhanced DNA fingerprinting.

In yet another aspect of this invention, it has been surprisingly discovered that the fluorescence signal obtained during the electronic denaturation of DNA hybrids is perturbed at or around electronic and power levels which are associated with dehybridization. Specifically, the fluorescence signal perturbation results in a rise or spike in fluorescence intensity prior to dehybridization of fluorescently labelled probes from a capture sequence attached to an APEX pad. The power level, amplitude and slope of this fluorescence spike provide analytical tools for diagnosis. The combination of the fluorescence perturbation with other measurements also indicative of the hybridization match/mismatch state, such as consideration of the electronic melting (50% fluorescence decrease during electronic stringency control) can in combination provide a more efficient and reliable hybridization match/mismatch analysis.

It is yet another aspect of this invention to provide for an improved DNA fingerprinting system using a microelectronic device. Such a device would be utilized to differentiate targets in the range from approximately 100 to approximately 3000 base pairs in size. Fluorescently labelled fragments having a given length would be attached to a capture probe at a test site. A reverse potential would be applied to the test site in an amount sufficient to determine the amount of binding between the capture probe and the labelled fragment. Generally, this would be by applying a reverse potential at increasing current so as to result in dehybridization of the targets at the site. Those DNA having longer length will be selectively dehybridized at lower electronic current levels. As such, the dehybridization current level correlates with DNA size.

Accordingly, it is an object of this invention to provide a system for the sample preparation, processing, hybridization, detection and analysis of biological materials.

It is yet a further object of this invention to provide a system that combines multiple steps or substeps within an integrated system.

It is yet a further object of this invention to provide for an automated DNA diagnostic system.

It is yet another object of this invention to provide for an improved fluorescence detection system, especially useful for small geometries.

It is yet another object of this invention to provide for an integrated, disposable combination of a fluidic system, such as a flow cell, and an active detection device.

It is yet another object of this invention to provide a system which is capable of manufacture using conventional techniques, with high efficiencies and low cost.

It is yet a further object of this invention to provide an improved DNA fingerprinting and analysis system which electronically discriminates between varying length DNA fragments.

DETAILED DESCRIPTION OF THE INVENTION

Figure 1:
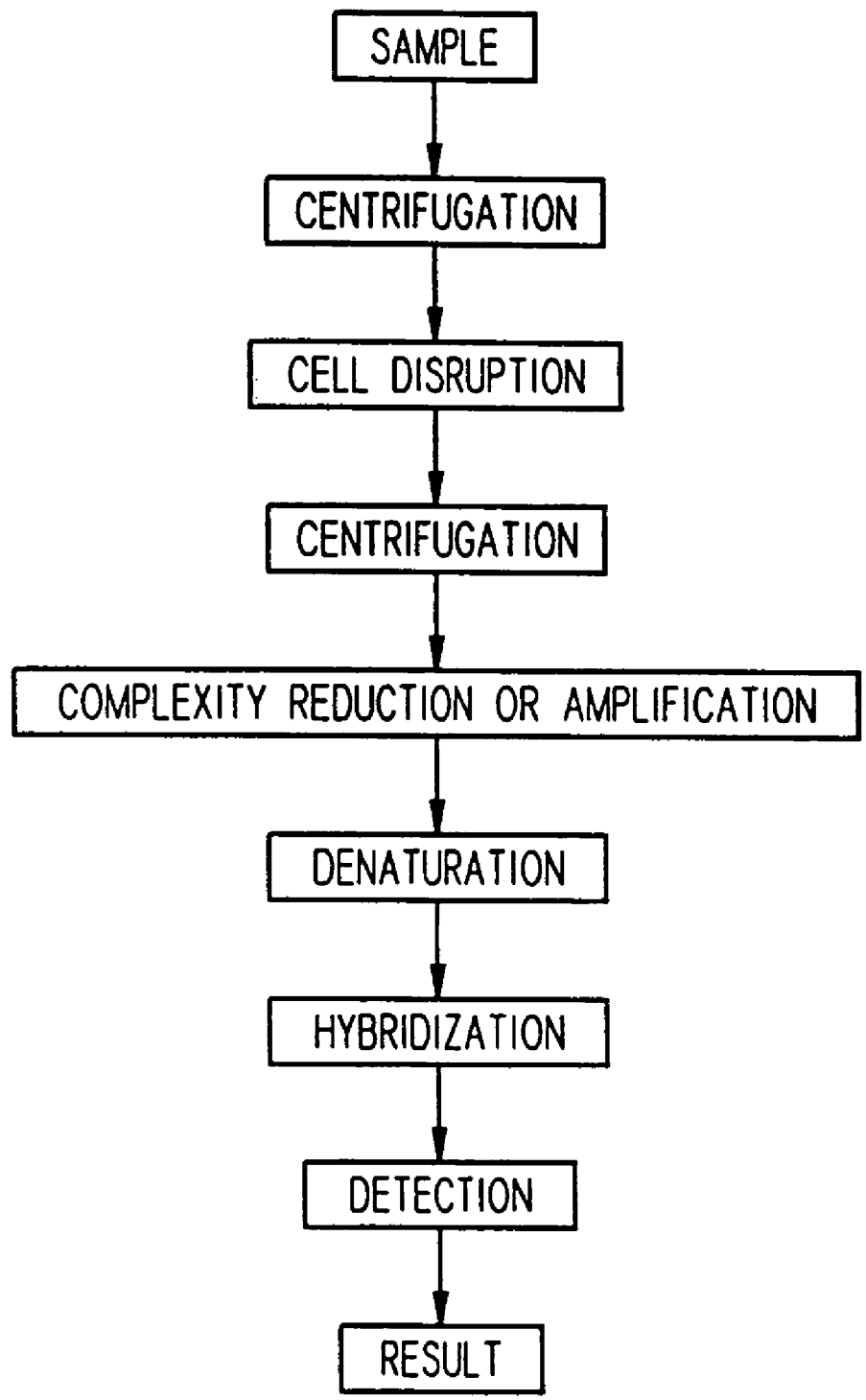
FIG. 1 shows the sequence of steps and substeps for sample preparation, hybridization and detection and data analysis.
Figure 2A:
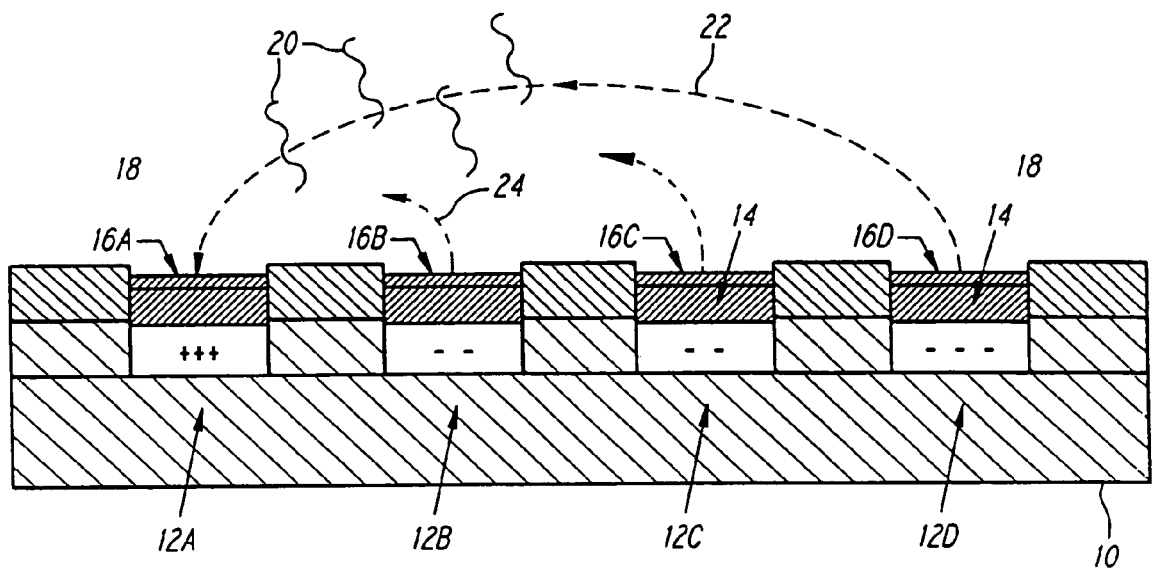
FIGS. 2A and 2B show the active, programmable matrix system in cross-section (FIG. 2A) and in perspective view (FIG. 2B).
Figure 2B:
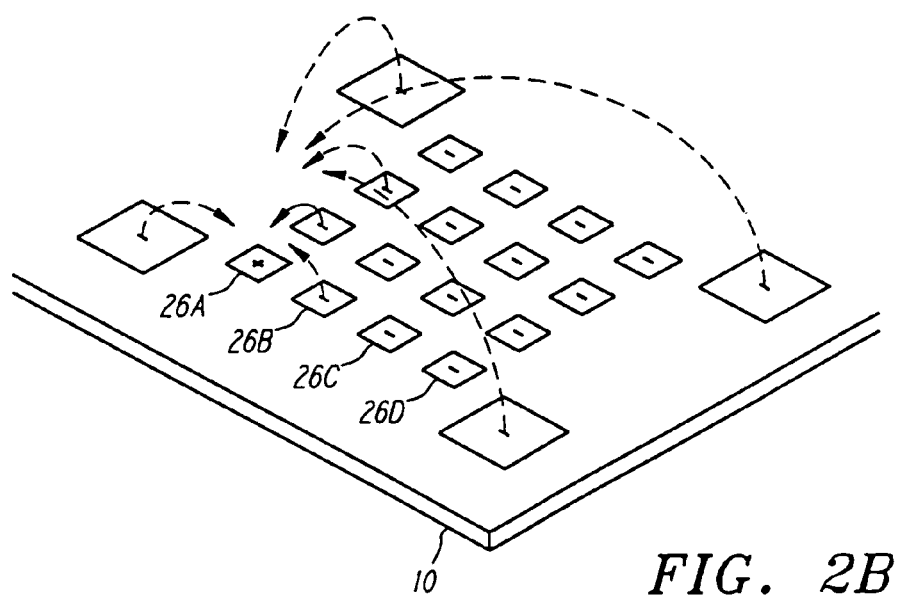

FIGS. 2A and 2B illustrate a simplified version of the active programmable electronic matrix hybridization system for use with this invention. Generally, a substrate 10 supports a matrix or array of electronically addressable microlocations 12. For ease of explanation, the various microlocations in FIG. 2A have been labelled 12A, 12B, 12C and 12D. A permeation layer 14 is disposed above the individual electrodes 12. The permeation layer permits transport of relatively small charged entities through it, but precludes large charged entities, such as DNA, from contacting the electrodes 12 directly. The permeation layer 14 avoids the electrochemical degradation which would occur in the DNA by direct contact with the electrodes 12. It further serves to avoid the strong, non-specific adsorption of DNA to electrodes. Attachment regions 16 are disposed upon the permeation layer 14 and provide for specific binding sites for target materials. The attachment regions 16 have been labelled 16A, 16B, 16C and 16D to correspond with the identification of the electrodes 12A-D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized snecific binding entity 20 becomes covalently attached to the attachment layer 16A.

The electrophoretic transport generally results from applying a voltage which is sufficient to permit electrolysis and ion transport within the system. Electrophoretic mobility results, and a current flows through the system, such as by ion transport through the electrolyte solution. In this way, a complete circuit may be formed via the current flow of the ions, with the remainder of the circuit being completed by the conventional electronic components, such as the electrodes and controlled circuitry. By way of example, for an aqueous electrolyte solution containing conventional material such as sodium chloride, sodium phosphate, buffers and ionic species, the voltage which induces electrolysis and ion transport is greater than or equal to approximately 1.2 volts.

It is possible to protect the attachment layers which are not subject to reaction, such as 16B and 16C by making their corresponding electrodes 12B and 12C. negative. This results in electrophoretic lines of force emanating from the attachment region 16B (only 16B will be discussed for simplicity, the results being similar for 16C). The electrophoretic force lines 24 serve to drive away negatively charged binding entities 20 from the attachment layer 16B and towards the attachment layer 16A. In this way, a "force field" protection is formed around the attachment layers 16 which it is desired to have nonreactive with the charged molecules 20 at that time.

One highly advantageous result of this system is that charged binding materials 20 may be highly concentrated in regions adjacent to signal attachment layers 16. As can be seen in perspective drawing FIG. 2B, if a individual microlocation 26A is positively charged, and the remaining microlocation are negatively charged, the lines of electrophoretic force will cause transport of the net negatively charged binding entities 20 toward the microlocation 26A. The microlocation 26A is intended to depict the combination in FIG. 2A of the attachment layer 16, the permeation layer 14 and the underlying associated electrode 12. In this way, a method for concentrating and reacting analytes or reactants at any specific microlocation on the device may be achieved. After the attachment of the specific binding entities 20 to the attachment layer 16, the underlying microelectrode 12 may continue to function in a direct current (DC) mode. This unique feature allows relatively dilute charged analytes or reactant molecules free in solution to be rapidly transported, concentrated, and reacted in a serial or parallel manner at any specific micro-location that is maintained at the opposite charge to the analyte or reactant molecules. This ability to concentrate dilute analyte or reactant molecules at selected microlocations 26 greatly accelerates the reaction rates at these microlocations 26.

After the desired reaction is complete, the electrode 12 may have its potential reversed thereby creating an electrophoretic force in the direction opposite to the prior attractive force. In this way, nonspecific analytes or unreacted molecules may be removed from the microlocation 26. Specific analytes or reaction products may be released from any microlocation 26 and transported to other locations for further analysis; or stored at other addressable locations; or removed completely from the system. This. removal or deconcentration of materials by reversal of the field enhances the discrimination ability of the system by resulting in removal of nonspecifically bound materials. By controlling the amount of now repulsive electrophoretic force to nonspecifically bound materials on the attachment layer 16, electronic stringency control may be achieved. By raising the electric potential at the electrode 12 so as to create a field sufficient to remove partially hybridized DNA sequences, thereby permitting identification of single mismatched hybridizations, point mutations may be identified.

Operations may be conducted in parallel or in series at the various attachment layers 16. For example, with reference to FIG. 2A, a reaction may occur first at attachment layer 16A utilizing the potentials as shown. The potential at electrode 12A may be reversed, that is, made negative, and the potential at the adjacent electrode 12B may be made positive. In this way, a series reactions occurs. Materials that were not specifically bound to attachment layer 16A would be transported by electrophoretic force to attachment layer 16B. In this way, the concentration aspect is utilized to provide high concentrations at that specific attachment layer then subject to the positive electrophoretic force. The concentrated materials may next be moved to an adjacent, or other, attachment layer 16. Alternatively, multiple attachment layers 16 may be deprotected in the sense that there is a net electrophoretic force field emanating from the electrode 12 through the attachment layer 16 out into the reservoir 18. By deprotecting multiple attachment layer 16, multiplex reactions are performed. Each individual site 26 may serve in essence as a separate biological "test tube" in that the particular environment addressed by a given attachment layer 16 may differ from those environments surrounding the other attachment layers 16.

Figure 3:
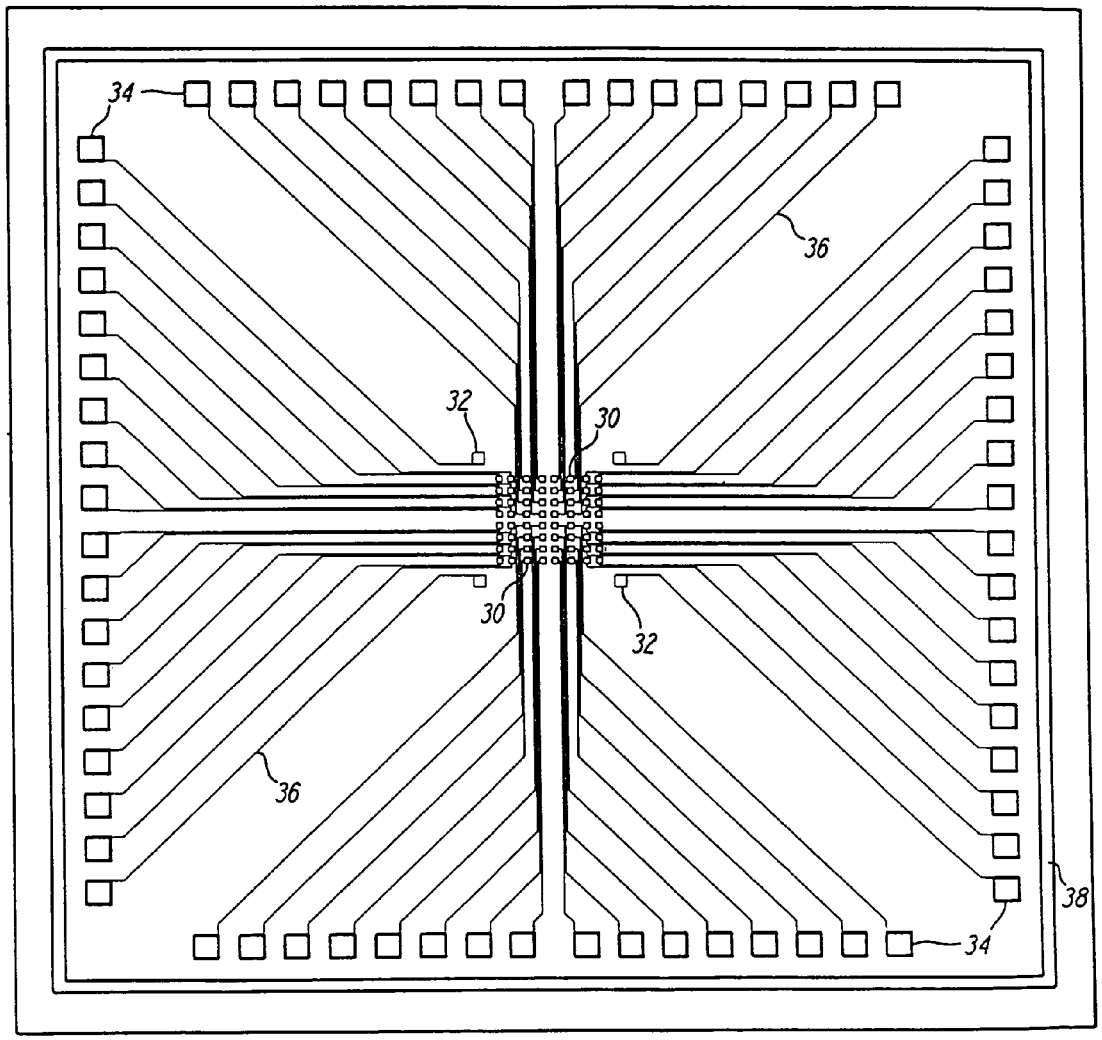
FIG. 3 shows the active, programmable matrix system structure at the metal mask layer.

FIG. 3 shows a plan view of the metal mask layer for an active programmable electronic matrix system. A plurality of individual electrodes 30 are formed preferably in an array. For example, an 8×8 matrix of individual electrodes 30 is formed. optionally, additional control or dump pads 32 may be provided to aid in generation of desired electrophoretic fields. The electrodes 30 and pad 32 are connected to contact pads 34. 68 contact pads 34 are shown corresponding to the 64 electrodes 30 and 4 pads 32. Leads 36 connect the electrodes 30 and pads 32 individually to the contracts 34.

As shown, a fan-out pattern is used to permit connections from the relatively condensed region of the electrodes 30 and pads 32 to the boundaries 36 of the mask.

Figure 4:
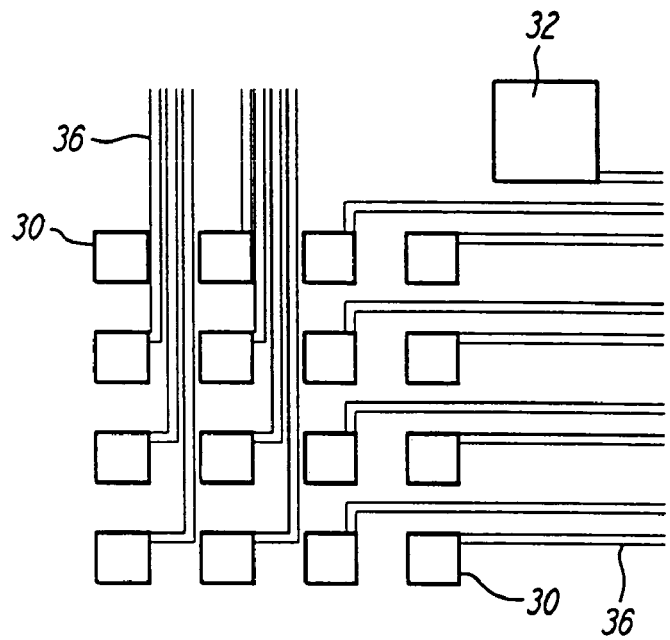
FIG. 4 shows detail of the active, programmable matrix system in plan view.

FIG. 4 shows an exploded detail plan view of the mask of FIG. 3. The resulting metallized system would appear substantially similar to the masked pattern. The electrodes 30 are shown formed as substantially square structures. The lead lines 36 connect the electrode 30 to the contact pad 34 (FIG. 3). The preferred line width of the lead 36 is 1 to 20 microns.

Figure 5:
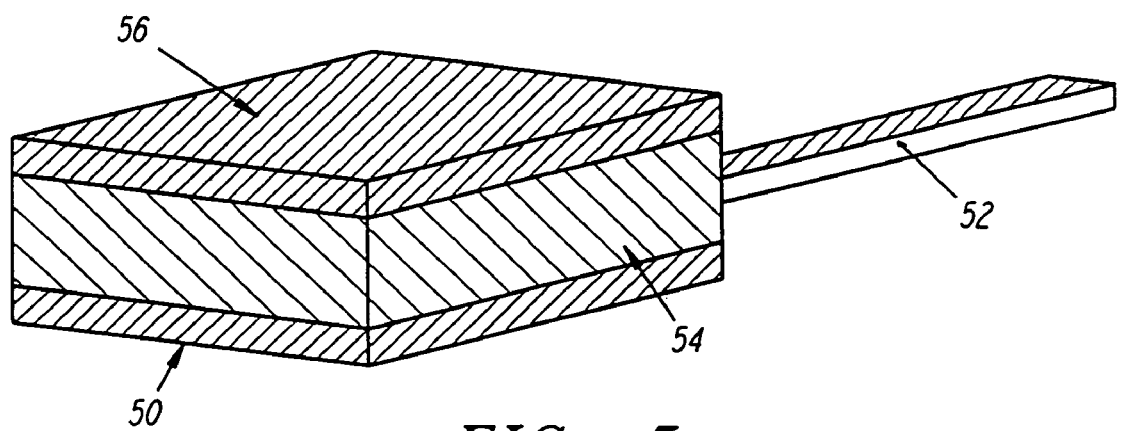
FIG. 5 shows a perspective view of a single microlocation and electrical connection.

FIG. 5 shows a perspective view of a single electrode 50. The electrode 50 is connected directly to the lead 52. A permeation layer 54 is disposed above the lead 50. An attachment layer 56 is disposed upon the permeation layer 54.

The permeation layer in microlithographically produced devices can range in thickness from 1 nm to 1,000 micrometers, with 500 nm to 100 micrometers being the most preferred. The permeation layer should cover the entire electrode surface. The permeation layer may be formed from any suitable material such as polymers, membranes, porous metal oxides (e.g., aluminum oxide), ceramics, sol-gels, layered composite materials, clays and controlled porosity glass.

Figure 6:
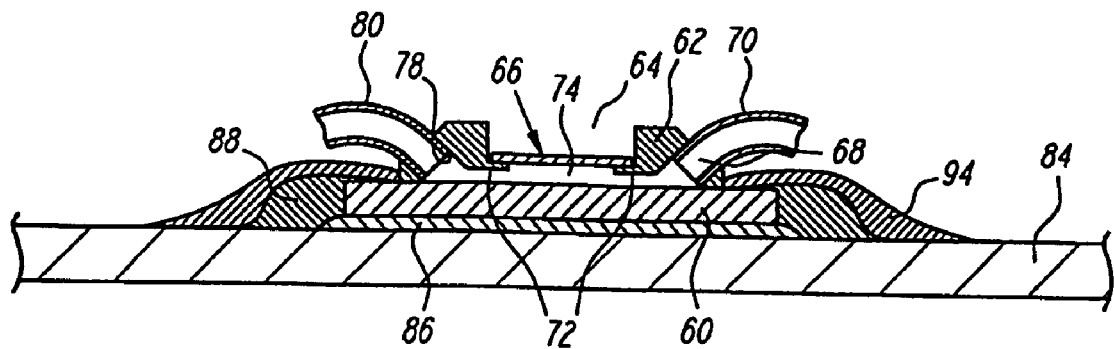
FIG. 6 shows a cross-sectional view of a fluidic system including a flow cell in combination with the APEX device.
Figure 7:
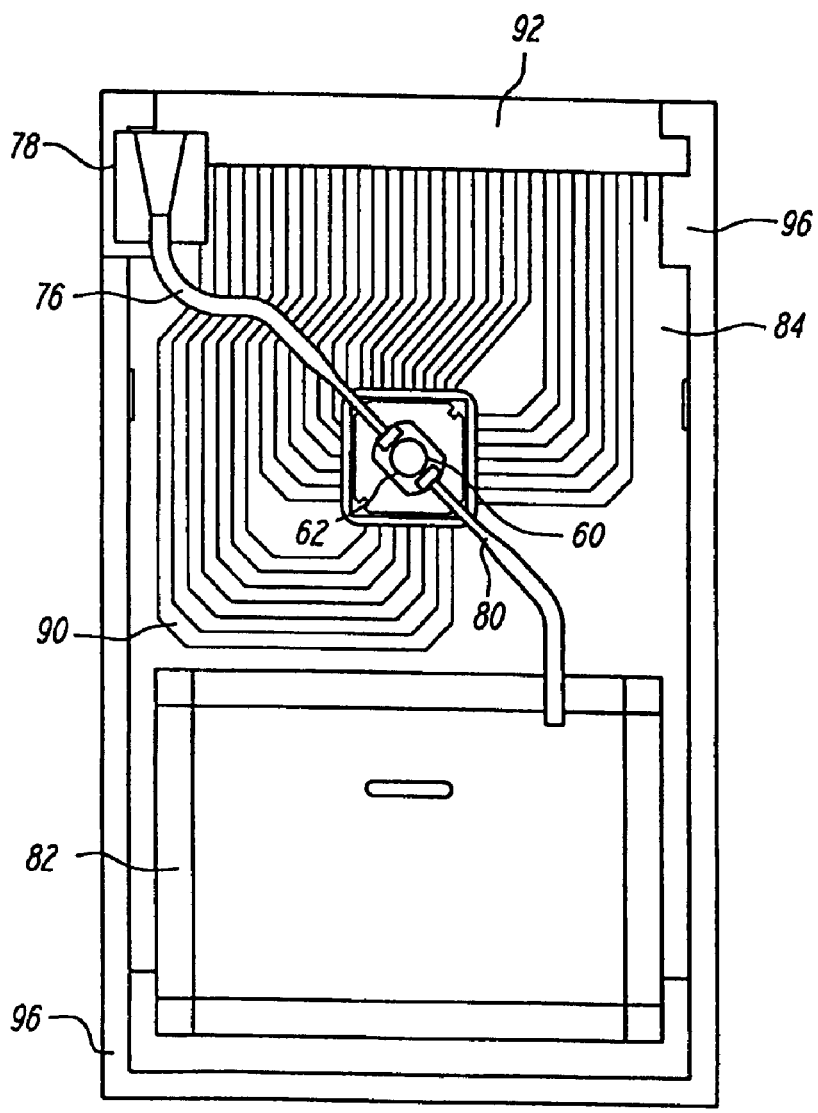
FIG. 7 shows a plan view of a fluidic system including a flow cell and liquid waste containment system in combination with the diagnostic system on a PCMCIA board.

FIG. 6 shows a cross-sectional view of a fluidic system in combination with a APEX like detection system. FIG. 7 shows a plan view of the fluidic system of FIG. 6 in the larger environment of its inclusion on a printed circuit board. Reference numbers will be utilized in comment to the extent possible. A biochip 60, preferably an APEX type chip as described above, is combined with a fluidic system. In the preferred embodiment, the fluidic system includes a flow cell 62. The flow cell 62 is disposed adjacent and above the biochip 60, and preferably in hermetic contact with the biochip 60. The flow cell 62 preferably includes an aperture 64 which permits optical access to the biochip 60. A flow cell window 66 contacts the flow cell 62 at the peripheral edges of the flow cell window 66. The flow cell window may be a quartz, or other suitable material chose in part for its transmission and non-fluorescence properties. Advantageously, the flow cell window 66 is chosen to have an index of refraction which substantially matches the index of refraction of the sample solution. An inlet port 68 and an outlet port 70 are provided through the flow cell 62. A sample chamber 74 is defined by the combination of the flow cell 62, the flow cell window 66 and the biochip 60. In the preferred embodiment, the sample chamber 74 has a volume from approximately 5 to approximately 10 microliters. An input tube 76 is preferably connected to the input port 68. Optionally, the input tube 76 connects to a fluidic interface port 78, such as formed by a female Luer taper system. An output tube 80 is preferably connected to the outlet port 70. The components of the fluidic system are preferably formed from inert materials, e.g., tetrafluoroethylene, or other medical grade plastics. The flow cell 62 and associated components may be formed through any known technique, such as molding or machining.

The output tube 80 preferably provides a communication path from the flow cell 62 to a reservoir 82. In the preferred embodiment, the reservoir 82 has a minimum volume of approximately 1.2 ml. As shown, the reservoir 82 is formed as a generally nonexpandable waste tube. In this embodiment, the waste tube reservoir 82 is filled by the fluid flow from the flow cell 62 through the output tube 80. In another embodiment, the reservoir 82 may be an expandable structure, such as an expandable mylar bag. The reservoir 82, may optionally operate under vacuum, thereby providing additional force to cause the sample to flow into the reservoir 82. Such a vacuum structure may be formed such as through a vacutainer.

The biochip 60 is preferably mounted on a printed circuit board 84, such as a FR4 circuit board, via adhesive 86. The adhesive 86 may be of any type conventional used in the surface mount technology art, and may be either conductive or nonconductive as desired. For example, the adhesive 86 may be a thermally conductive epoxy. Lead wires 88 connect from the biochip 60 to the printed leads 90. Conventional techniques such as ball bonding or wedge bonding using 0.001 inch AlSi or gold wire may be used. The printed leads 90 are formed on the printed circuit board through conventional techniques. As shown in FIG. 7, the printed circuit board is formed in the PCMCIA format, such that a 68 position electrical contact 92 provides an interface between the printed leads 90 and the electronics connected to the electrical contact 92. Other conventional formats may be used.

Preferably, the lead wires 88 are potted or encapsulated in a protective material 94, such as nonconductive UV resistant epoxy. Preferably, the protective material 94 provides electrical insulation for the lead wires 88, provides a moisture barrier for the lead wires 88 and provides mechanical support for overall device ruggedness. Overall rigidity of the printed circuit board 84 and structures formed thereon is generated by the optional frame 96.

With regard to the preferred mode of construction of the. structure of FIGS. 6 and 7, the biochip 60 is preferably attached via adhesive 86 to the printed circuit board 84. Next, lead wires 88 are connected from the biochip 60 to the printed leads 90. The lead wires 88 are then encapsulated in the protective material 94, with the central region of the biochip 60 disposed out-ward from the adhesive 86 being kept clear. In the APEX device the clear region is approximately 7.5 mm$^2$. The flow cell 62 is then directly bonded to the biochip 60. In the preferred embodiment, the flow cell 62 may be formed of any material compatible with the purposes and materials described, such as medical grade plastic. The biochip 60 may be formed, such as from silicon. The flow cell 62 may then be attached to the silicon of the biochip 60 by adhesives, which would generally be relatively thin. The order of affixing the flow cell 62 to the biochip 60 and the encapsulating of the lead wires in the 88 in the protective material 94 may be reversed, namely the flow cell 62 or components thereof may be affixed to the biochip 60 prior to the addition of the protective material 94.

Preferably, the biochip 60 is placed at the center of rotational gyration of the structure of FIG. 7. In certain embodiments, the biochip 60 includes a permeation layer or other layer disposed at the surface of the biochip 60. These materials are often spin-coated onto the surface of the biochip 60. By placing the biochip 60 at the axis of. rotation, the completed structure of FIG. 7, excluding the flow cell window 66, and optionally excluding other components, e.g., the frame 96, the input tube 76, the fluidic interface port 78, the output tube 80 and the reservoir 82, may be spun so as to add the materials to the surface of the biochip 60. Since the spin rates can often be relatively large, for example, 10,000 rpm for the spin-coating of certain polymers, placing the biochip 60 at the center of rotation provides for easier spin-coating. By forming the spun on structures, such as a permeation layer and capture sequences, a generic device of the type shown in FIG. 7 may be formed, and the suitable polymers and capture sequences for an assay placed down as desired. Additionally, by forming the assay related layers on the biochip 60 after substantially all other structures have been formed permits the precleaning of a manufactured device prior to the addition of the biologically sensitive materials_ such as the permeation layer and the attachment sequences.

Figure 8:
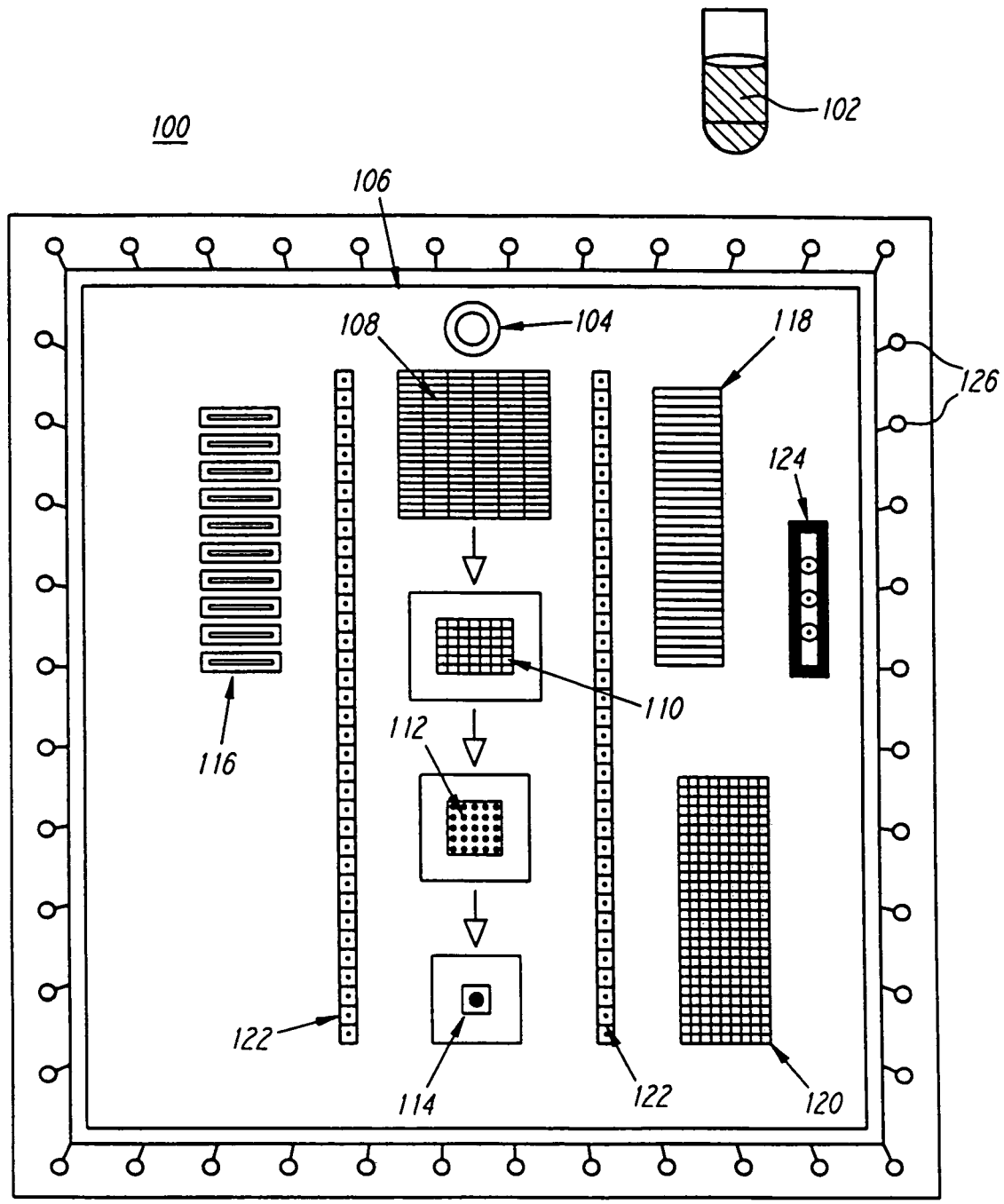
FIG. 8 shows a plan view of the system including an electronic cell sorter matrix, DNA selectors and restriction fragment selectors and hybridization matrix.

FIG. 8 shows a complete system 100 for the automated sample preparation and hybridization of prepared materials. A sample 102, such as blood or other biological materials are introduced into the system 100. Generally, a sample addition port 104 is provided. Generally, the sample addition port 104 is utilized when an overlying biological containment structure is present such that the sample 102 could not be directly placed into the system without access via the port 104. Optionally, a containment cover 106, such as glass or transparent plastic, may be disposed over the system 100.

Sample preparation is performed in this system 100 by the combination of the electronic cell sorter matrix component 108 and DNA selector component 110 and restriction fragment selector component 112. The selector component 112 may be further characterized based upon its intended use, such as a restriction fragment selector 112 or to isolate bacterial or viral nucleic acids from human genomic or background DNA. The electronic cell sorter matrix component 108 consists of underlying electrodes, with permeation layers and an attachment layers. These effectively form a matrix of locations for the attachment of cells. Generally, the area for individual locations and the complete matrix area are larger than the areas in an analytical device component. Thus, the electronic cell sorter matrix is scaled appropriately to accommodate variation in the number of cells from different samples and sample sizes. The attachment layers can be generally selective for cells, or individual selective for different types of cells. Optionally, groups or sets of locations can be made selective for one type of cell. Cell selectivity can be imparted by attaching specific antibodies or cell adhesion factors to the attachment layer. The matrix 108 operates by free field electrophoresis.

The crude DNA selector 110 and selector 112 serve to bind the crude DNA output from the electronic cell sorter matrix 108 and permit selective cleavage of the desired DNA from the bound material. The term crude is used merely to denote a non-final stage in DNA isolation or complexity reduction. The DNA is bound to the selector in a region which is believed not to contain the desired DNA material. The desired DNA materials are then severed from the bound materials, such as by application of restriction enzymes. In the case of infectious disease analysis, the selector 112 would be designed to isolate bacterial or viral nucleic acids from human genomic or other background DNA. The severed, unbound material is then physically moved from the crude DNA selector 110 to the selector 112. Preferably, electrophoretic transport is used to remove the severed material. This process may be repeated by binding the severed material to a selector, upon which a restriction enzyme acts so as to cleave the unbound portion which contains the desired DNA.

For example, human DNA contains approximately 100, 000 genes. Of the total DNA material, a significant portion constitutes repeating sequences which do not contain the desired DNA information. The DNA may be bound to a selector by these noninformation bearing repeating sequences. The bound DNA may be severed from the unbound DNA which is believed to contain the desired DNA-to be analyzed. This process may then be repeated with yet more specific sequences causing binding of the material to the selector.

The output of the selector 112 is then supplied to the APEX chip 114. Operations on the matrix 114 are performed as described in connection with FIGS. 2A and 2B.

An electronic reagent dispenser system 116 may be 35 provided to deliver reagents to the system 100. Preferably, the reagents are delivered by electrophoretic force if they are charged. Optionally, an electronic waste disposal system 118 is included within the system 100. The waste disposal system 118 attracts charged waste particles to it and disposes of them by holding the charged entities on it. Another optional member of system 100 is the DNA fragment storage system 120. This fragment storage system 120 serves to temporarily hold DNA fragments for future analysis.

Optionally, auxiliary electrodes 122 may be provided in the system 100. The auxiliary electrodes 122 may assist in the electrophoretic motion of materials throughout the system 100. By providing selective activation of the auxiliary electrodes 122 along the long axis, the motion of the materials may be aided or inhibited.

In addition to the sample injection port 104, other inputs and outputs beyond the system 100 may be optionally included. For example, fluid input and output ports 124 serve to provide additional addition of fluids to the system 100. Further, electrical connections 126 are shown disposed around the system 100 and serve to provide electrical contact, such as to the driver board/computer interface 138 (FIG. 9).

The system 100 may include some or all of the functions described above. For example, the combination of sample preparation in the form of complexity reduction, as performed by the DNA selector 110 and restriction fragment selector 112 may be associated with the analytical matrix 114. However, any or all of the above described functions may be combined as desired.

Figure 9:
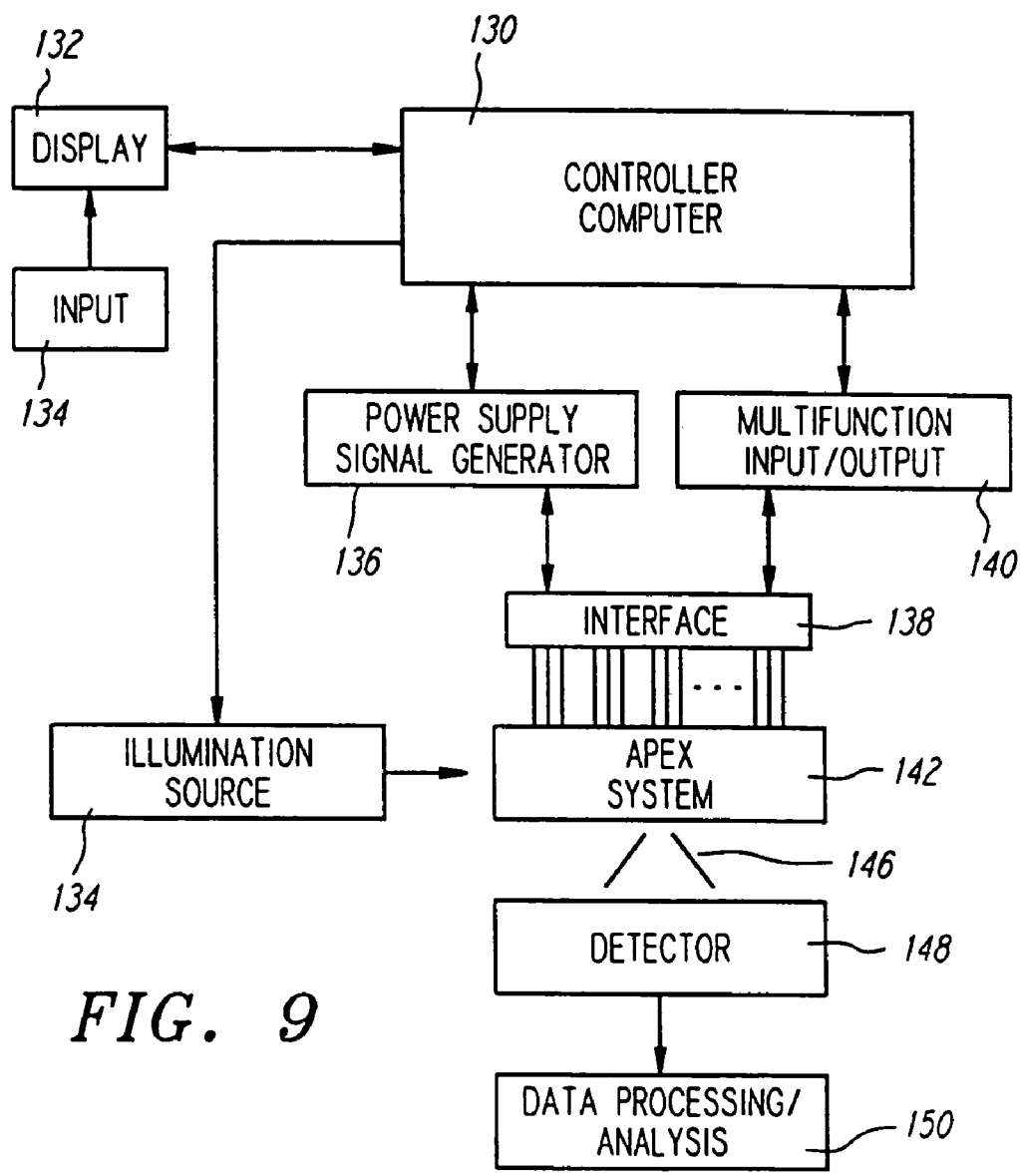
FIG. 9 shows a block diagram description of the control system.

FIG. 9 shows a block diagram of the overall system including the controller 130. The underlying electrodes in an APEX device are made active by the application of a controlled potential to the electrode or by the sourcing of a controlled current through the electrode. Full functionality is realized when the potential or current at each electrode of the APEX device is independently controlled. This is accomplished by an APEX controller system.

The controller computer 130 interfaces with user input/output devices, such as a display 132 and input device 134. The display 132 may be any form of conventional display such as a monitor or computer screen. The input 134 may be any conventional user input device, such as a keyboard, mouse, or touch-screen device. The controller computer 130 is connected with the power supply and waveform generator 136. The controller 130 sets the power supply and waveform generator 136 to provide the current or voltage output to the interface 138. In the preferred embodiment, the power supply or waveform generator 136 is capable of providing precisely regulated and voltage and current sourcing. The controller computer 80 provides control signals to the interface 138 via the multifunction input/output board 140. The interface 138 provides a simplified connection to the contacts for the APEX system 142.

The interface preferably includes relays that permit selective connection between the power supply and waveform generator 136 to the specific electrodes of the APEX system 142. In one embodiment, the interface 138 comprises a plurality of relays which connect the power supply and waveform generator 136 to the APEX system 142 electrodes. The connections permit the selection or nonselection of a path between the power supply and waveform generator 136 to the APEX system 142 electrodes. Additionally, another relay permits selecting the polarity of the voltages supplied to the APEX system 142 electrodes. Optionally, if multiple source levels are available, such as from a multiple output power supply 136, the specific level to be connected to an APEX system 142 electrode may be set independently of those for the other electrodes.

Thus, as described in connection with FIG. 2A, by placing certain electrodes (e.g., 12B and 12C) at a negative, but lesser potential than electrode 12D, the attachment region 16B and 16C would be protected by the local force field.

The interface 138 may serve to select the desired voltage for the individual electrodes in the APEX system 142. Alternatively, such a different voltage arrangement may be achieved through use of a voltage divider.

In the preferred embodiment, the controller computer 130 is a Macintosh Quadra 950. National Instruments Corporation LabVIEW software is used to provide a software interface for a user to program the devices connected to the APEX and to collect and process data from an assay. National Instruments NuBus boards are used to provide the hardware interface from the Quadra 950 computer 130 to the power supply devices 136 that source potentials and currents and that measure the actual currents and potentials and the results of the assay.

The user controls the assay through a Virtual Instrument created with the LabVIEW software. The virtual instrument provides a user friendly graphical representation of the controls that the user may exercise, and of some of the results of applying these controls to the APEX device to perform an assay. The user interfaces with the Virtual Instrument through the keyboard and mouse (collectively, input 134) of the Quadra 950 computer 130. The Virtual Instrument provides software interfaces to a National Instruments NB-MIO-16XL multi-purpose input/output 140 and to a National Instruments OMA2800 board that are connected to the NuBus data bus of the Quadra 950.

The multipurpose I/O board is able to provide digital and/or analog signals to external devices to implement the programmed sequence specified by the user through the Virtual Instrument. The MIO board is also able to digitize and store in the Quadra 950, under control of the Virtual Instrument, signals generated by the devices connected to the APEX. The DMA2800 provides MIO board through Direct Memory Access, bypassing the Quadra 950 CPU. The DMA 2800 also provides a GPIB (IEEE 488) interface for control of external devices that adhere to the IEEE 488 communication and data transfer standard, which includes most modern instruments.

In this preferred embodiment of the controller, two external devices are used to source the potentials or currents to the APEX. A Keithley 236 Source/Measure Unit power supply 86 provides adequate stability and flexibility as a source of precisely regulated potential or current. The SMU 236 either applies a potential and measures the resultant current or provides a source of current and measures the resultant potential. This device is programmed from the Virtual Instrument under GPIB control through the DMA2800 board to control the current or potential levels and time dependence, and to measure and store the actual potentials and currents that are sourced to the APEX.

The sourced currents or potentials are applied to the APEX through an array of relays in interference 138 that provide independent switching of each electrode between no connection, connection to positive source and connection to negative source. The preferred embodiment also provides for more than one Source/Measure supply to be utilized to provide different levels of positive and negative potential or current to different electrodes. The array of relays is provided by a National Instruments SCXI Chassis with nine 16-channel, Class 3 Relay Modules connected in the chassis, providing a total of 144 relays. Two relays are used per electrode to provide for electrode disconnected or electrode connected to either positive or negative source. In the preferred embodiment, a bundle of cables connects these relays to the APEX device through a Cerprobe Probe Card that provides mechanical contact of probes to the bond pads of the APEX device.

The controller computer 130 optionally controls the illumination source 144 for excitation of fluorescence to detect DNA hybridization. In the preferred embodiment, the illumination source 144 is a laser which outputs radiation at an appropriate wavelength to excite fluorescent markers included within the APEX system 142.

The output of the APEX system 142 is passed through observation path 146 to the detector 148. The observation path 146 may be a physical connection, such as through a fiber optic, or may comprise an optical path such as through a microscope. Optical filters may be utilized in the observation path to reduce illumination of the detector at wavelengths not corresponding to the emission spectra of the fluorescent markers in the APEX system 142. Additionally, notch filters may be utilized as necessary to reduce illumination of the detector 148 at the excitation wavelength of the laser illumination source 144. The detector 148 may optionally form an image of the APEX system 142, such as through the use of a cooled CCD camera. In addition to, or as an alternative to, forming an optical image, the emitted fluorescence radiation from the APEX system 142 may be detected by conventional means such as photodiodes or photomultiplier tubes. The output of the detector 148 is provided to the data processing/analysis system 150. This system monitors the level of detected probe material in the APEX system 142. Optionally, an expert system may be utilized in the analysis system 150.

In the preferred embodiment, a Data Translation Frame Grabber board is interfaced to the Quadra 950 NuBus, to provide capture to memory of images recorded by video cameras such as the Optronics cooled color CCD camera used in the preferred embodiment. This CCD camera observes the APEX device through a microscope with appropriate filters to provide visualization of fluorescence on the APEX array.

Alternate systems may implement all the functionality of the controller as described, but may use custom devices incorporated into printed circuit boards and custom software to control the board with a similar user-friendly interface for programming the device. These alternate systems may also incorporate the switching elements of the array of relays into a semiconductor device underlying the active, programmable matrix system.

The permeation layer (e.g., layer 14 of FIG. 2) may be formed from materials such as, but not exclusive to, membranes, metal oxides (e.g., aluminum oxide), carbon chain polymers, carbon-silicon chain polymers, carbon-phosphorous chain polymers, carbon-nitrogen chain polymers, silicon chain polymers, polymer alloys, layered polymer composites, interpenetrating polymer materials, ceramics, controlled porosity glass, materials formed as sol-gels, materials formed as aero-gels, materials formed as hydro-gels, porous graphite, clays or zeolites.

Permeation layers separate the binding entities from the surface of the electrode. Micro-locations have been created using microlithographic and micro-machining techniques. The permeation layer may be disposed within a well (see, e.g., FIG. 2A) or may not be recessed and simply be coated with a permeation layer covering the electrodes. Either of these arrangements may be formed by spin coating of the permeation layer. Chemical modification of the surface of the micro-locations and of polymer layers over the micro-locations have been used to create specialized attachment sites for surface functionality.

Mesh type permeation layers involve random arrangements of polymeric molecules that form mesh like structures having an average pore size determined by the extent of cross-linking. We have demonstrated the formation of mesh type permeation layers using several nolvmerizable formulations containing acrylamide as a monomer. We have used triethylene glycol diacrylate, tetraethylene glycol diacrylate and N,N'-Methylene-bisacrylamide as cross-linking agents. Poly-l-lysine with molecular weights of 330 kilodaltons and 25 kilodaltons was mixed into the acrylamide/copolymer formulation to provide a means for attaching specialized functionality to the surface of the permeation layer. The mixture was cast onto the surface of the micro-location. It was then photopolymerized by ultraviolet light. In some cases, AuC14 was added as a photoinitiator. The polymer formulations were cast from water and the nonaqueous solvents, methanol, tetrahydrofuran, acetonitrile, acetone, and mixtures of these solvents.

DNA capture probe was attached to the surface of the permeation layer by a Schiff base reaction between an oxidized ribonucleoside attached to the DNA capture probe and the primary amine of the poly-l-lysine. This provides evidence of covalent attachment of special functionality to the surface of the permeation layer.

An oxidized DNA capture probe was brought to a surface micro-location by electrophoretic transport. The capture probe was labeled with a fluorescent marker. This demonstrates the ability to address a micro-location by electrophoretic transport.

An oxidized capture probe with a fluorescent marker attached was attracted to the surface of the permeation layer at a micro-location by electrophoretic transport. The permeation layer was removed from the micro-location by mechanical means. No evidence of the presence of the fluorescently labeled capture probe was observed. This demonstrates the ability of the permeation layer to protect the DNA from the electrode surface.

The maximum DC current density that was attained at a gold micro-location, which was not modified with a permeation layer, before bubbles due to water hydrolysis appeared was 8 milliampheres/cm2. The maximum DC current density that was attained at a gold micro-location, which was modified by an acrylamide-based permeation layer, before bubbles due to water hydrolysis appear was 40 milliampheres/cm2. This demonstrates the ability of the permeation layer to raise the maximum accessible current density before bubbles form due to water hydrolysis.

An ionomer sandwich permeation layer is formed from one or more lamina of polyelectrolytes. The polyelectrolyte layers may have the same charge, different charge, or may be charge mosaic structures.

A two layer ionomer sandwich layer was formed from a base layer of a perfluorinated sulfonic acid polyelectrolyte (Nafion) and an upper layer of poly-l-lysine. The base Nafion layer was cast onto a micro-location and allowed to dry. This base layer was then exposed to a 1% by weight aqueous solution of poly-l-lysine. The cationic lysine-based polymer adsorbed strongly to the anionic Nafion base layer. The poly-l-lysine layer allowed the attachment of an oxidized DNA capture probe to the surface of the permeation layer by a Schiff base reaction. The Nafion base layer-is anionic and is perm-selective toward negative ions such as DNA.

Figure 10:
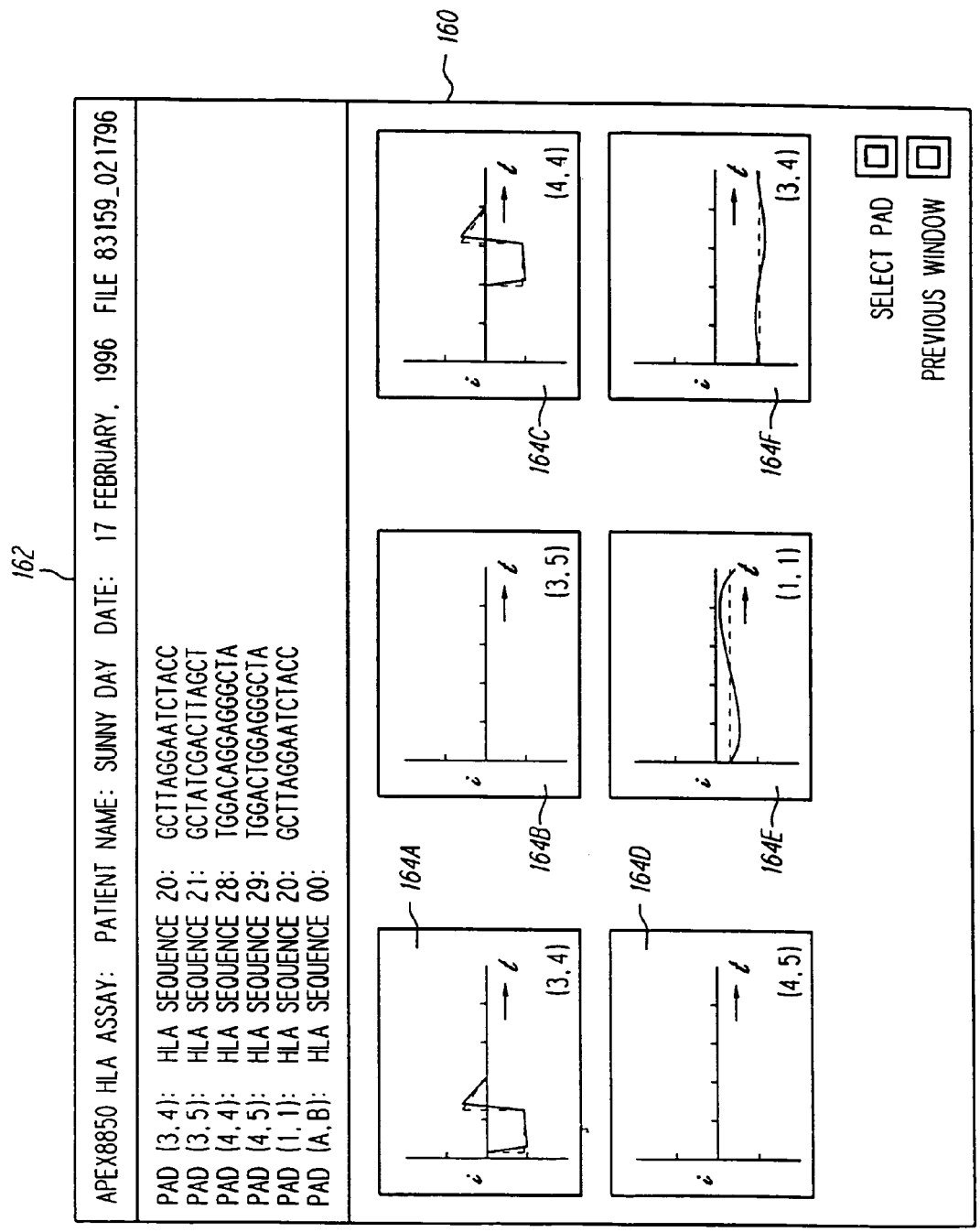
FIG. 10 shows user displays for various voltage and current regimes.

FIG. 10 shows examples of the graphical user interface. Window 160 shows an overall view of the display. Identification information 162 is provided. The various pads of the active, programmable matrix system are identified in a rectangular coordinate system. The displays 164 each show the electrical parameter, such as current or voltage for particular pads. Box 164A shows the current as a function of time for a pad, (3,4), wherein the current varies as a function of time, changing directions during the course of the application. Box 164B shows a pad, (3,5), having no applied current during the time shown. Box 164C shows a time varying current for pad (4,4), wherein that current is delayed with respect to time relative to the pad (3,4) reported in Box 164A. Box 164D shows a pad, (4,5), with no applied current as a function of time. Box 164E shows a pad, (1,1), for which the voltage has a constant, negative DC value. Box 164F shows the voltage as a function of time for a pad, (3,4) having a more negative DC value. In all cases, the boxes show the programmed current or voltage as a dotted line, and the measured current or voltage as a solid line.

In addition to the preferred embodiment of the invention and the alternatives described above, several more alternatives are possible. For example, the electric field that gives rise to ion migration may be modulated in time as long as a DC bias voltage or current is applied simultaneously. The use of an AC signal superimposed on a DC bias voltage or current can achieve three things, 1) minimize the background due to nonspecifically bound DNA, 2) provide a means of electronic stringency control where the control variable is the frequency of the alternating current or voltage, 3) provide a means of aligning DNA molecules spatially.

Many alternatives to the detection of hybridized DNA by fluorescence exist. Most of the alternative techniques also involve modification of capture or target or reporter DNA probes with reporter groups that produce a detectable signal. A few of these techniques based on purely physical measurements do not require reporter groups. These alternative techniques are catalogued as follows: (1) Linear Optical Methods including fluorescence, time modulated fluorescence, fluorescence quenching modulation, polarization selective fluorescence, absorption, specular reflectance, changes in index of refraction, ellipsometry, surface plasmon resonance detection, chemiluminescence, speckle interferometry and magneto-optic Kerr effect; (2) Nonlinear Optical Methods including second harmonic generation, third harmonic generation, parametric mixing, optical heterodyne detection, phase conjugation, solution damping and optical Kerr effect; (3). Methods Based on Thermal Effects including differential scanning calorimetry, multifrequency differential scanning calorimetry, and differential thermal analysis; (4) Methods Based on Mass Changes including crystal microbalances, cantilever microbalances, surface acoustic waves and surface Love waves; (5) Electrochemical Methods including amperometry, coulometry, voltammetry, electrochemiluminescence, charge transfer in donor-acceptor complexes and surface impedance spectroscopy; and (6) Radioactivity Detection Methods using labeled groups.

Figure 11:
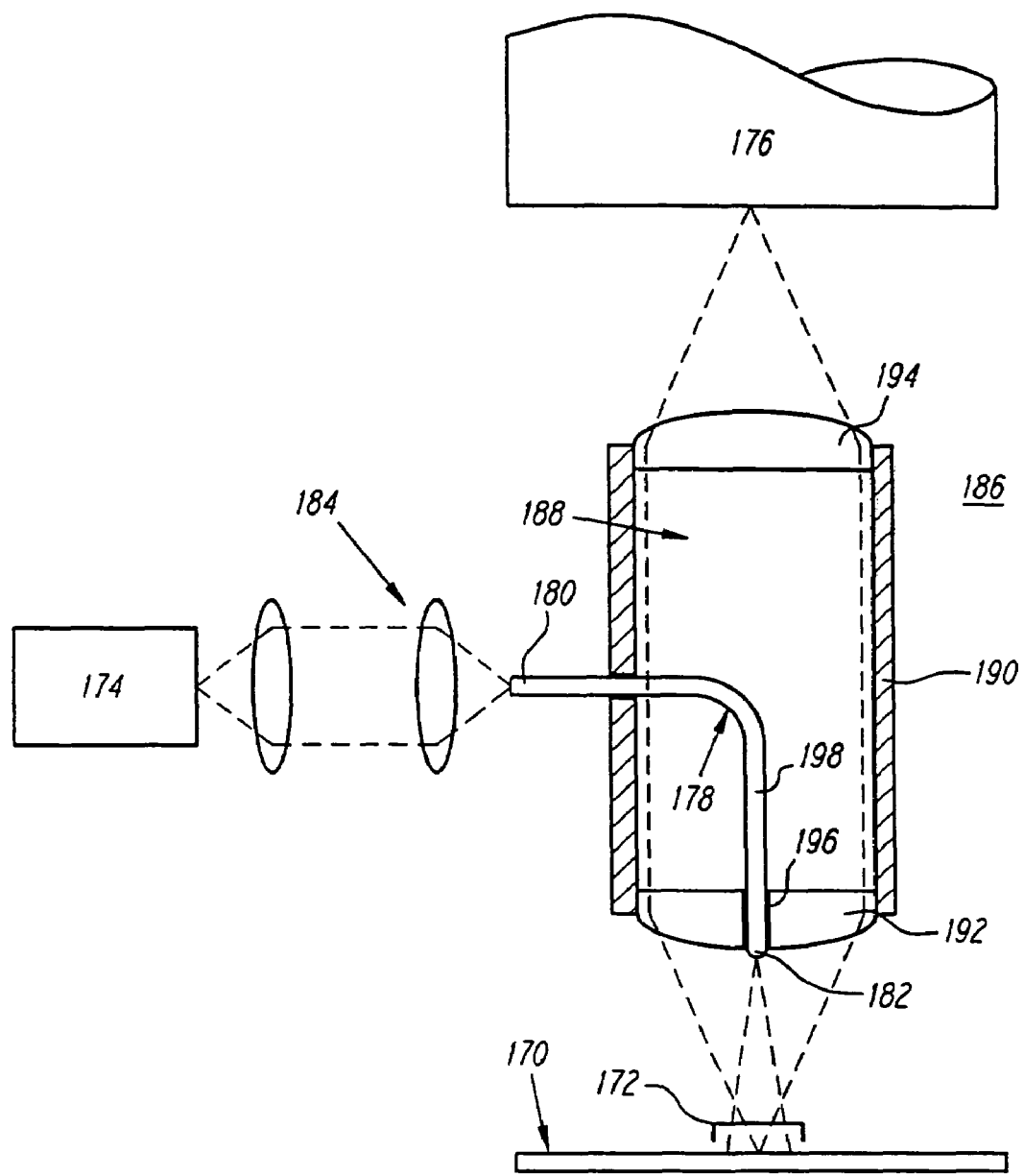
FIG. 11 shows a cross-sectional view of a fluorescence detection system useful for small geometry systems.

FIG. 11 shows a cross-sectional view of an improved detection system. A sample 170 includes a region of interest 172. The region of interest 172 may include multiple areas on the sample 170. Any of the various excitation sources 174 and detectors 176 as are conventionally used in fluorimetric systems may be utilized with this invention.

Delivery of energy from the excitation. source 174 to the region of interest 172 is preferably accomplished via a excitation fiber 178. The excitation fiber 178 is preferably fiber optic light guide. The excitation fiber 178 has an input end 180 and an output end 182. The output end 182 may be formed in a manner as known to those skilled in the art so as to provide focused projection of the energy from the excitation source 174.

Optional fiber launch system optics 184 receive the output of the excitation source 174 and provide the radiation to the input end 180 of the excitation fiber 178.

Radiation emanating from the region of interest 172 (shown as dashed lines between the region of interest 172 and detector 176) is passed through light guide 186. The light guide 186 preferably comprises a liquid light guide portion 188. The liquid light guide 188 is surrounded by a housing 190, which serves to contain the liquid light guide 188. A proximal lens 192 is disposed within the housing 190 at that portion of the light guide 186 which is disposed towards the region of interest 172. A distal end 194 is disposed within the housing 190 at the end of the light guide 186 disposed towards the detector 176.

In the preferred embodiment, the excitation fiber 178 is formed coaxially in the light guide 186. Preferably, the output end 182 of the excitation fiber 178 is disposed through aperture 196 in the proximal lens 192. In this manner, the radiation from the excitation source 174 may be supplied through the excitation fiber 178 and delivered to the region of interest 172 without passing through the optical components of the proximal lens 192. Alternatively, the output end 182 of the excitation fiber 178 may be disposed within the liquid light guide 188 such that the radiation of the excitation source 174 passes through the optical component of the distal lens 194 before being supplied to the region of interest 172. The use of the excitation fiber 178, such as when a fiber optic, permits a degree of mechanical decoupling between the excitation source 174 and the sample 170. For example, the excitation source 174 and the detector 176 may be fixed in place while the light guide 186 and excitation fiber 178 are moved over the, sample 170. Preferably, the excitation fiber 178 includes an axially region 198 which is disposed along the axis of rotation of the light guide 186. This concentric axial alignment of the optical paths of the axial region 198 of the excitation fiber 178 and the light guide 186 provide for alignment to the detector 176. The liquid light guide 188 advantageously provides for more complete transference of the energy from the region of interest 172 to the detector 176. Alternatively, fiber bundles may be utilized in the light guide 186, though the liquid light guide 188 provides more complete coverage of the output from the proximal lens 192.

The APEX device as described previously has been utilized in novel ways resulting in method which improve the analytical or diagnostic capabilities of the device. It has been surprisingly discovered that the fluorescent signal is perturbed during the electronic denaturation of DNA hybrids. This method has particular application to DNA hybridization and single-base mismatch analysis. Specifically, during electronic denaturation, also known as stringency control, a rise or spike in the fluorescence intensity has been observed just prior to the dehybridization of the fluorescent labelled probes from capture sequences attached to the APEX chip pad.

Figure 12A:
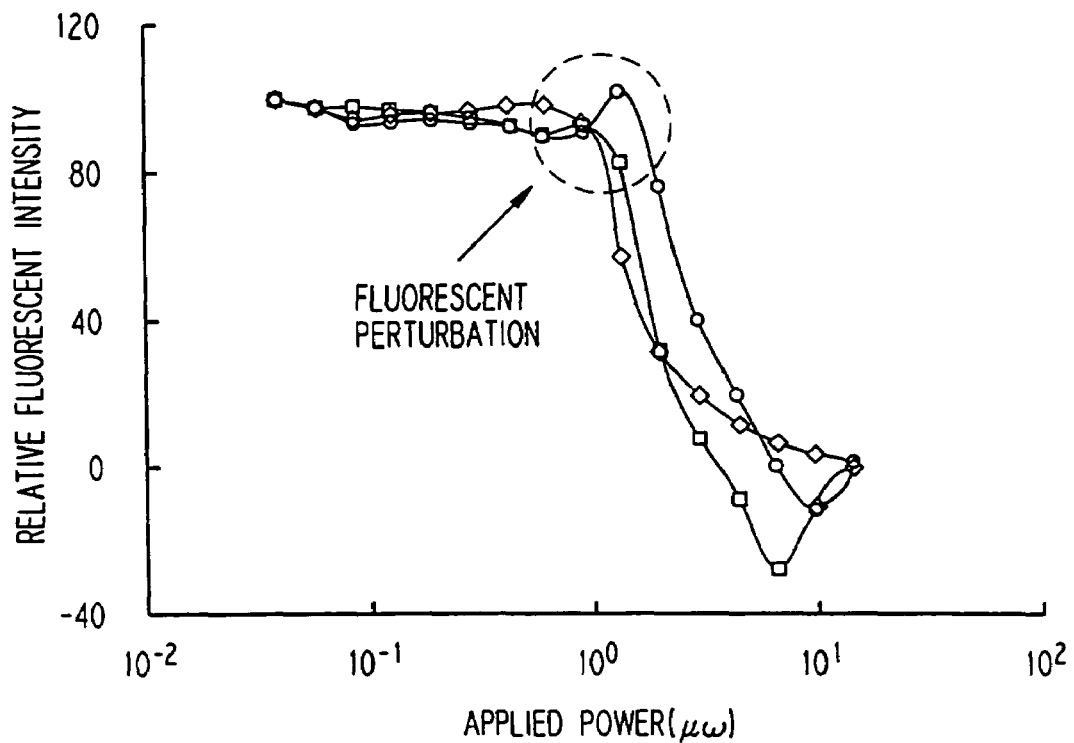
FIG. 12A is a plot of the relative fluorescent intensity as a function of applied power (microwatts) for a 20-mer oligomer duplex (100 k AT).
Figure 12B:
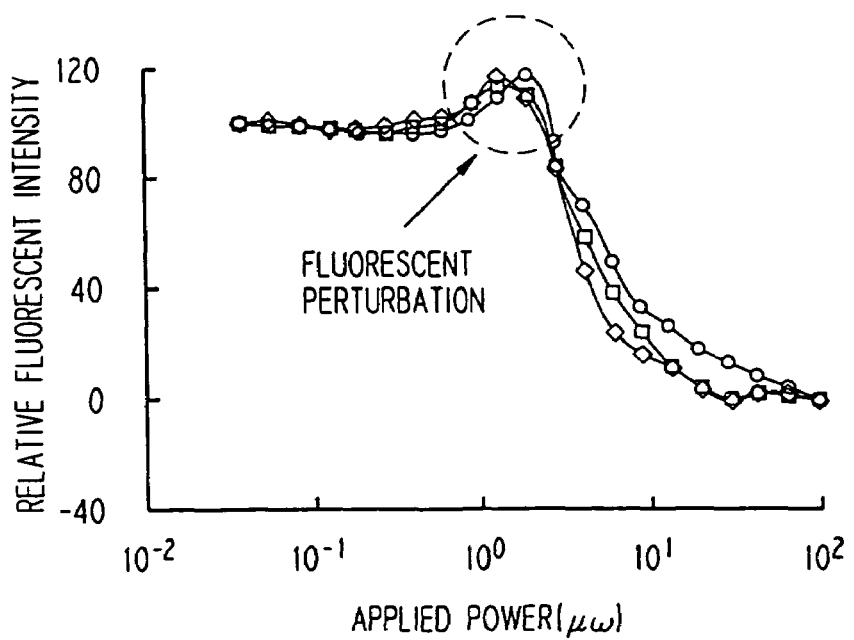
FIG. 12B is a plot of the relative fluorescent intensity versus applied power (microwatt) for a 19-mer oligomer duplex (53% GC).

FIGS. 12A and 12B show the results of electronic denaturization experiments run on an APEX chip having 25 test microlocations with 80 micron diameter utilizing platinum electrodes. For this use, the chip was overlaid with a 1 micro thick avidin/agarose permeation layer. Two 5'-labeled bodipy Texas Red (Ex 590 nm, EM 630 nm) target probes were used in the experiments. The probe of FIG. 12A was a 20 mer (5'-BYTR-AAATTTTAATATATAAT-3'), (Seq. ID No. 1) containing 100% AT, with a melting temperature (Tm) of 33° C. The probe of FIG. 12B was a 19 mer (5' BYTR-CCACG-TAGAACTGCTCATC-3'), (Seq. ID No. 2) containing 53% CG, with a melting temperature (Tm) of 54° C. (Melting temperature or Tm refers to the temperature at which the dehybridization process is 50% complete). The appropriate complementary biotinylated capture sequences were attached to the avidin/agarose permeation layer over several of the test pads (on the same chip). The capture probe density was $\sim 10^8$ probes per pad. The fluorescent labeled target probes, at a concentration of $\sim 1.0$ M in 50 mM sodium phosphate (pH 7.0), 500 mM NaCl were first hybridized to the attachment probes on the 5580 chips. The chips were then thoroughly washed with 20 mM NaPO4 (pH 7.0).

Electronic denaturation was then carried out by biasing the test pad negative, and increasing the power to the test pad from $\sim 10^{-1}$ microwatts ($\mu W$) to $\sim 2 \times 10^2$ microwatts (uW) over a 90 second time period. Three pads were tested for each of the target probes. The relative change in fluorescent intensity was plotted as a function of the increasing power. In general, the electrophoretic force or power necessary to dehybridize a probe from its complementary sequence correlates with the binding energy or Tm (melting temperature) for the DNA duplex. In above experiments the overall power level (SW) necessary to dehybridize the 19-mer probe with 53% GC probe (Tm of 54° C.) was higher than for the 20-mer probe with 100% AT (Tm of 33° C.), that is, the equivalent electronic melting point (Em) at which dehybridization is 50% complete is higher for the 53% GC probe. Also, the fluorescent perturbation (FIGS. 12A and 12B, circled region) for the 10-mere probe with 53% GC is observed to be significantly different from that associated with the 100% AT probe.

Figure 13A:
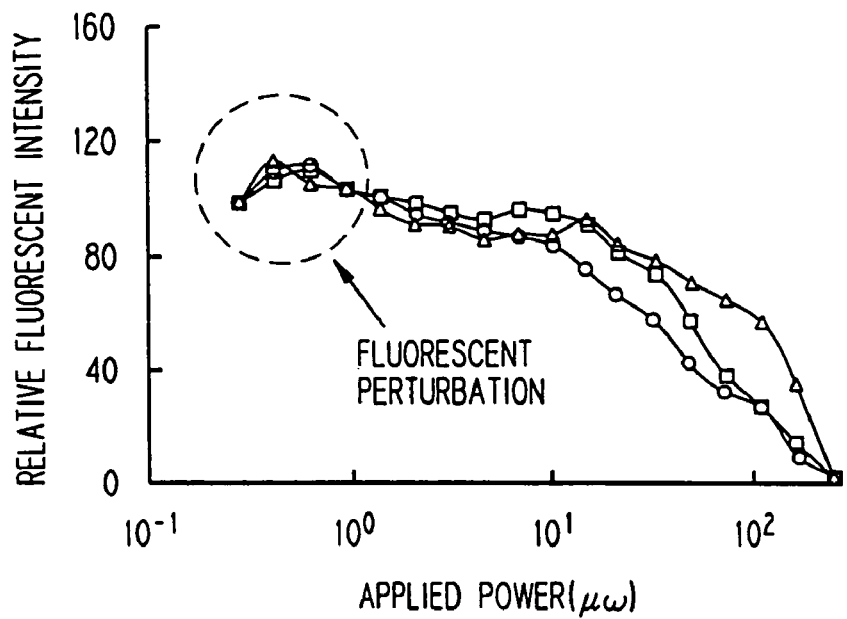
FIG. 13A is a graph of the relative fluorescent intensity versus applied power (microwatt) for a 20-mer oligomer duplex (100% AT).
Figure 13B:
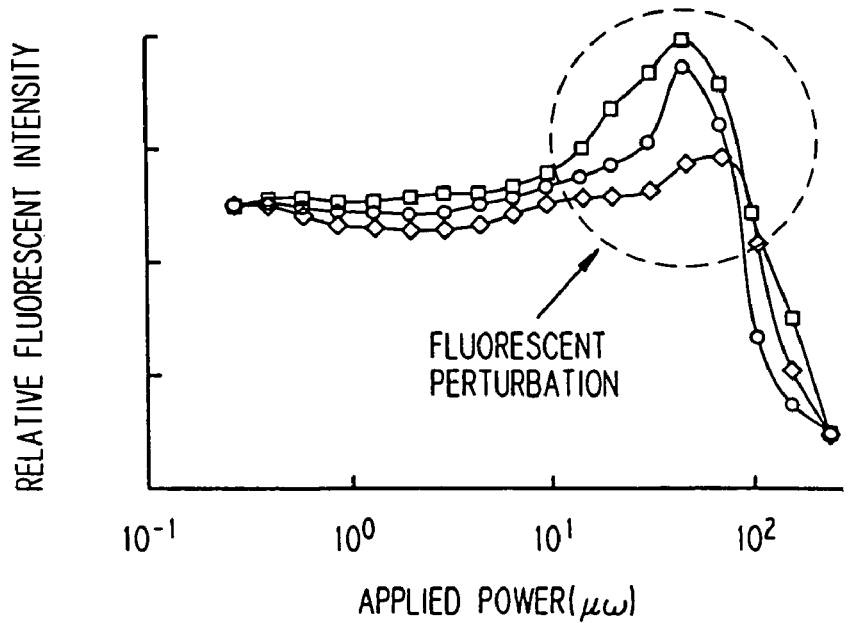
FIG. 13B is a plot of the relative fluorescent intensity versus applied power (microwatt) for a 19-mer oligomer duplex (53% GC).

FIGS. 13A and 13B show the results of denaturation experiments run on the APEX chip having 25 test microlocations with 20 micron deep wells to the underlying platinum electrodes. The well structures on the chip were filled with avidin/agarose composite, forming a 20 micron deep permeation layer. The same fluorescent target probes, capture probes and protocols were used in the deep well experiments as in the operation of the device resulting in the information of FIGS. 12A and 12B. As in the first experiments, the overall power (μW) necessary to de-hybridize the 19-mer probe with 53% GC (Tm of 54° C.), is higher than for the 20-mer probe with 100% AT (Tm of 33° C.). Also, the slope for the 100% AT probe is much shallower, then for the 53% GC probe. The fluorescent perturbation/spike phenomena is very, pronounced for the 19-mer probe with 53% GC in the deep well experiments.

The fluorescent perturbation phenomena correlates well with the sequence specificity of the dehybridization process. The power level (SW) value, amplitude and slope of the fluorescent spike are useful for many aspects of hybridization analysis including single base mismatch analysis. The fluorescent perturbation (Fp) value, namely those values associated with the fluorescence perturbation, e.g., onset value, peak height and slope, combined with the electronic melting (Em) values, namely, the half-height value of fluorescence, provide significantly higher reliability and additional certainty to hybridization match/mis-match analysis. By combining two or more analytical measurements, a more effective and precise determination may be made.

In the above experiments, the target probes were labeled with a Bodipy Texas Red fluorophore in their 5' terminal positions. While Bodipy TR is not a particularly environmentally sensitive fluorophore it nevertheless showed pronounced effects during electronic denaturation. More environmentally sensitive fluorophores may be used to obtain larger perturbations in their fluorescent properties during electronic de-hybridization.

Figure 14A:
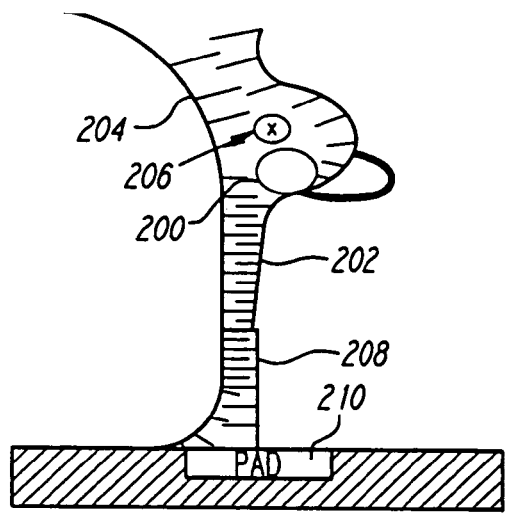
FIG. 14A shows a cross-sectional view of a mismatched test site having a capture probe, target DNA and a reporter probe.
Figure 15A:
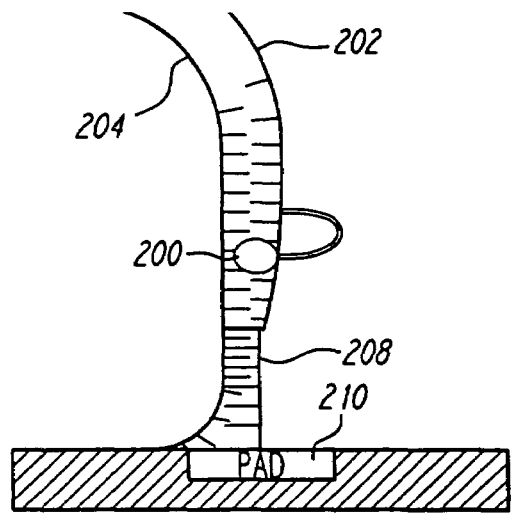
FIG. 15A is a cross-sectional view of a matched test site having a capture probe, target DNA and a reporter probe with an intercalated fluorophore.

The placement of a sensitive fluorescent label in optimal proximity to the initial denaturation site is preferred. By associating the fluorescent label in proximity to the denaturation site, as opposed to labelling at the end of the target or probe, increased specificity and enhanced effect may result. As shown in FIGS. 14A and 15A, an intercalcating fluorophore 200 may be disposed between a reporter probe 202 and target DNA 204. FIG. 14A shows the condition in which the reporter probe 202 is mismatched from the target DNA 204 by a mismatched base 206. In each of FIGS. 14A and 15A, the capture probe 208 serves to capture the target DNA 204, with the pad 210 providing the electrophoretic action. Preferably, the intercalcating fluorphore 200 would be placed next to the single base mismatch site 206 (FIG. 14A). The intercalcating type fluorescent label could be, for example, ethidium bromide or acridine. or any other known fluorescent labels consistent with the objects of this device and its use.

Figure 14B:
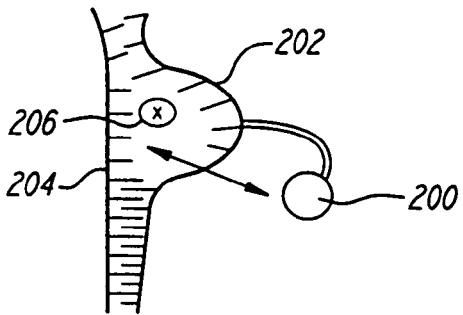
FIG. 14B is a cross-sectional view of target DNA and a reporter probe with a associated fluorophore.
Figure 15B:
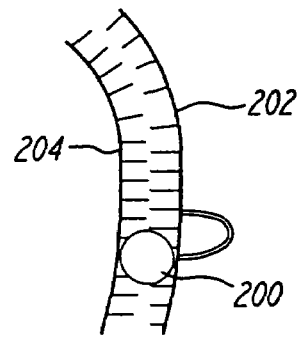
FIG. 15B is a cross-sectional view of target DNA and a reporter probe with an intercalcating fluorophore.

FIGS. 14B and 15B show the condition of the reporter probe 202, the target DNA 204 and the mismatch base site 206 after the application of a pulse at the fluorescent perturbation value via the pad 210. The change from intercalated to the non-intercalated environment would produce a major change in fluorescent signal intensity of the label.

Figure 14C:
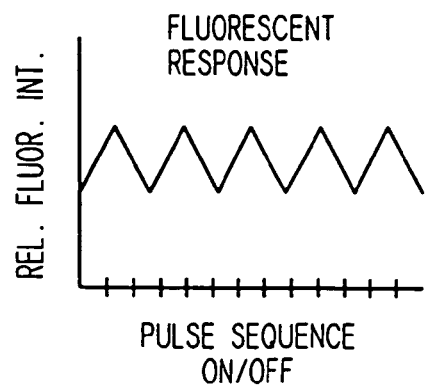
FIG. 14C is a graph of the fluorescent response graphing the relative fluorescent intensity as a function of time for a pulsed sequence.
Figure 15C:
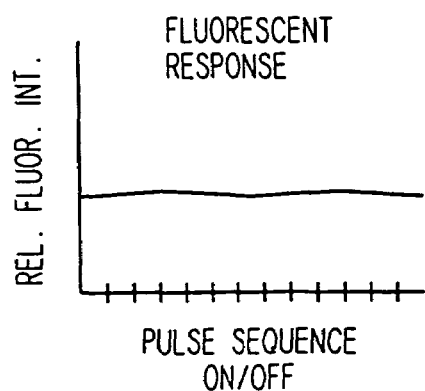
FIG. 15C is a graph of the fluorescent response showing the relative fluorescence intensity as a function of time for a pulsed sequence.

Furthermore, the use of a mis-match site directed fluorophor label does not require that the hybrid be completely denatured during the process. As shown in FIG. 14C and FIG. 15C, an analysis procedure is preferred in which an appropriate pulsed "Fp" power level is applied which causes a mismatched hybridization site to partially de-nature and re-nature relative to a matched hybridization site. The procedure results in an oscillating fluorescent signal being observed for mismatch hybrid site, while the fluorescent signal for the matched hybrid site remains unchanged. FIGS. 14C and 15C shows the relative fluorescent intensity as a function of varied applied power. This procedure provides a highly specific and discriminating method for single base mismatch analysis. Additional advantages include: (1) Longer probes (>20-mer) than those used in conventional hybridization procedures can be used in this process, (2) Probe specificity is more determined by placement of the fluorescent label (particularly for single base mismatches), and (3) as the procedure does not require complete denaturation of the hybrid structures, each sample can be analyzed repetitively for providing a higher statistical significant data, such as through standard averaging techniques.

The electronic stringency device disclosed herein may be advantageously used for DNA fingerprinting and analysis. An electronically addressable array measures DNA fragment sizes by determining the different electronic force necessary to dehybrize the fragment of varying lengths from capture probe sequences. As shown in FIG. 16A-D, three test sites 210 are shown labelled test sites A, B and C. This number of test sites may be greatly increased in an actual device, but three are shown for demonstration of the principle and technique. Capture probes 212 would be attached to the test sites 210 through the techniques described above. Fragments of a given, though likely unknown, first length 214 would be hybridized with the capture probe 212 at test site C 210. A second fragment 216 having presumably a different length than fragment 214 is hybridized to capture probe 212 at test site B 210. Similarly, a fragment 218 having a presumably different length than fragments 214, 216 is hybridized to capture probe 212 at test site A 210.

Figure 16A:
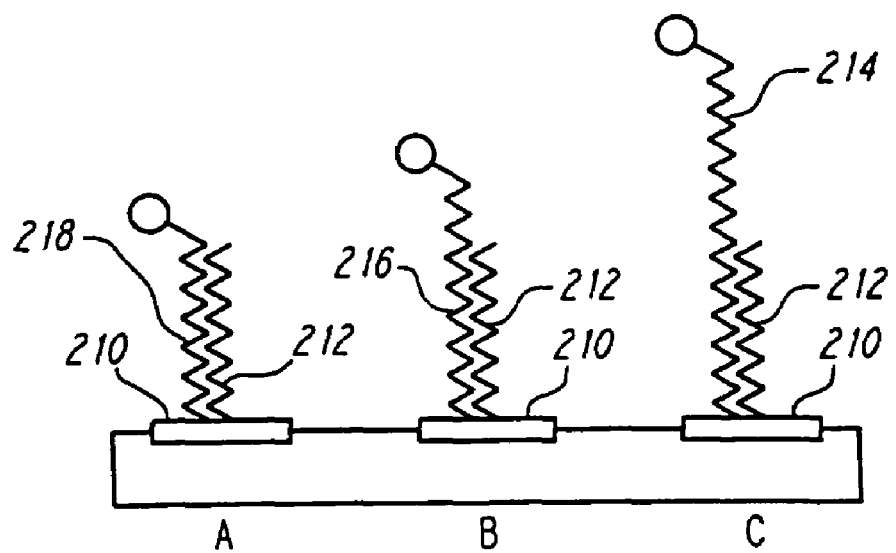
FIG. 16A-D are cross-sectional views of multiple test sites of a electronic stringency control device utilized for DNA fingerprinting and analysis.
Figure 16B:
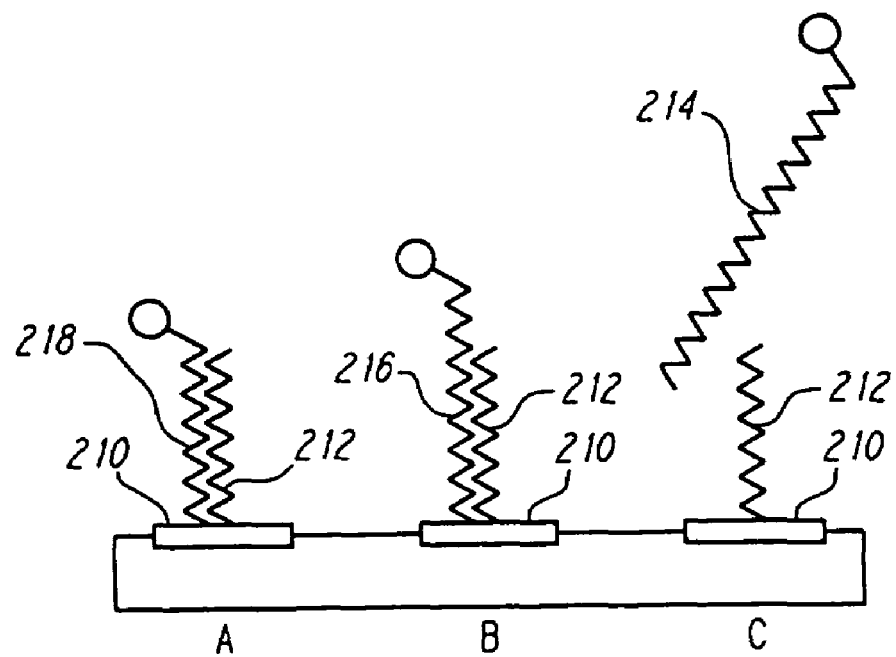
Figure 16C:
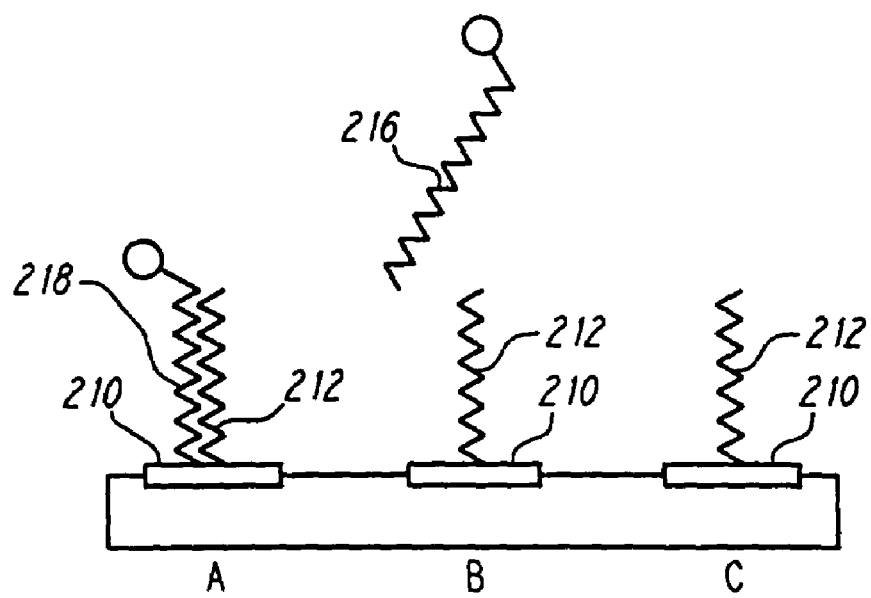
Figure 16D:
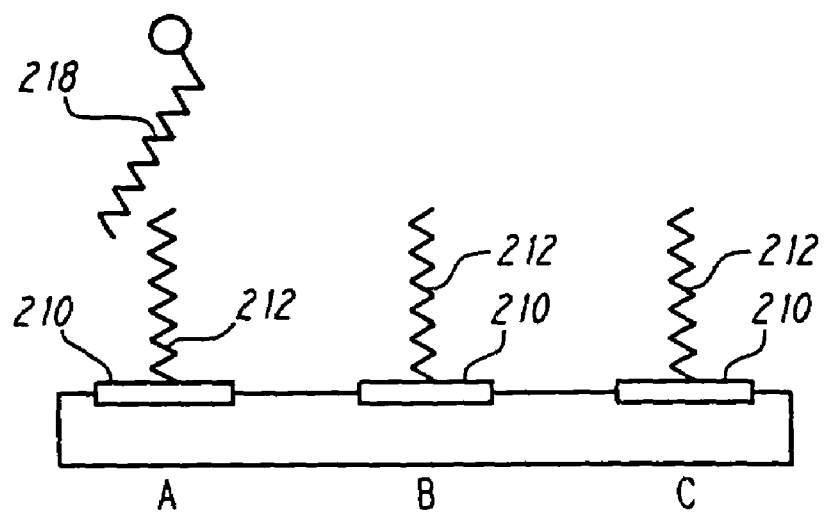

The test sites 210 are then subject to reverse potential at increasing current levels. The fluorescence from the test sites 210 is monitored. As the reverse potential is increased, indications of dehybridization are detected, such as by observing the peak as described in connection with FIGS. 12A, 12B, 13A and 13B, or by complete dehybridization. In the preferred embodiment, the complete dehybridization of the fragments 214, 216 and 218 are detected from the capture probes 212. Since the varying length fragments 214, 216 and 218 have different lengths, they will have different amounts of net charge. Thus, as the potential at test sites 210 is increased, those fragments 214, 216 and 218 having larger net charge will be subject to larger force, and accordingly, be removed from the test site 210 at a lower potential. FIG. 16B shows the condition in which the test site C 210 has reached or exceed a reverse potential which caused the dehybridization of the fragment 214 from the capture probe 212. Next, as shown in FIG. 16C, when the reverse potential at test site 210 reaches that level at which the fragment 216 is subject to sufficient force to dehybridize from capture sequence 212, the fragment 216 separates from test site B 210. Finally, as the reverse potential is increased even further, the shortest fragment 218 is removed from the capture sequence 212 at test site A 210. In this way, the electric potential or current required to resolve different sized fragments from each test site is determined and correlated with the fragment size.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

an interface unit coupled to the output of the power supply and waveform generator, wherein the interface includes a plurality of relays which couple the output of the power supply and waveform generator selectively to the microlocations of the array of microlocations, wherein the controller provides control signals to the interface so that the relays are under control of the controller, and wherein the controller directs the relays to select the polarity of the voltages applied to the microlocations, to permit selection or nonselection of a path from the power supply and waveform generator to the microlocations, and to select an amount of potential or current provided to the microlocations.

The invention claimed is:

1. An active biological device having an array of microlocations, including at least a first microlocation and a second microlocation, the device adapted to receive a solution including one or more charged entities, the device comprising:
   a controller, wherein the controller is a computer;
   a power supply and waveform generator, the power supply and waveform generator adapted to output a DC bias and superimposed AC signal at an output under control of the controller; and 2. The device of claim 1 wherein the DC bias is a current bias.

3. The device of claim 1 wherein the DC bias is a voltage bias.

4. The device of claim 1, wherein the AC signal is non-repetitive.

5. The device of claim 1 wherein the AC signal is zero at time zero.

* * * * *